US012372528B2

(12) United States Patent
O'Donovan et al.

(10) Patent No.: US 12,372,528 B2
(45) Date of Patent: Jul. 29, 2025

(54) MARKERS FOR THE EARLY DETECTION OF COLON CELL PROLIFERATIVE DISORDERS

(71) Applicant: Freenome Holdings, Inc., South San Francisco, CA (US)

(72) Inventors: Brian D. O'Donovan, San Francisco, CA (US); Shivani Mahajan, San Francisco, CA (US)

(73) Assignee: Freenome Holdings, Inc., South San Francisco, CA (US)

( * ) Notice: Subject to any disclaimer, the term of this patent is extended or adjusted under 35 U.S.C. 154(b) by 0 days.

(21) Appl. No.: 18/163,149

(22) Filed: Feb. 1, 2023

(65) Prior Publication Data
US 2023/0243830 A1 Aug. 3, 2023

Related U.S. Application Data

(63) Continuation of application No. PCT/US2021/052816, filed on Sep. 30, 2021.

(60) Provisional application No. 63/087,728, filed on Oct. 5, 2020.

(51) Int. Cl.
*G01N 33/574* (2006.01)
*G01N 33/68* (2006.01)
*G16B 35/00* (2019.01)

(52) U.S. Cl.
CPC ... *G01N 33/57419* (2013.01); *G01N 33/6854* (2013.01); *G16B 35/00* (2019.02)

(58) Field of Classification Search
CPC ......... G01N 33/57419; G01N 33/6854; G16B 35/00
See application file for complete search history.

(56) References Cited

U.S. PATENT DOCUMENTS

| | | | |
|---|---|---|---|
| 5,786,146 | A | 7/1998 | Herman et al. |
| 7,270,960 | B2 | 9/2007 | Hellstrom et al. |
| 7,727,720 | B2 | 6/2010 | Dhallan |
| 7,754,429 | B2 | 7/2010 | Rigatti et al. |

(Continued)

FOREIGN PATENT DOCUMENTS

| | | |
|---|---|---|
| EP | 2444811 A1 | 4/2012 |
| EP | 3193173 A1 | 7/2017 |

(Continued)

OTHER PUBLICATIONS

Asmus et al. Simultaneous Targeted Methylation Sequencing (sTM-Seq). Curr Protoc Hum Genet 101(1):e81, pp. 1-19 doi:10.1002/cphg.81 (2019).

(Continued)

*Primary Examiner* — Karlheinz R. Skowronek
*Assistant Examiner* — Emilie A Neulen
(74) *Attorney, Agent, or Firm* — WILSON SONSINI GOODRICH & ROSATI

(57) ABSTRACT

Systems, media, compositions, methods, and kits disclosed herein relate to a panel of autoantibody biomarkers for the early detection of colon cell proliferative disorders, including colorectal cancer. The presence or levels of the autoantibodies in a biological sample for the autoantibody panels described herein may be used for classifier generation, and as inputs in machine learning models useful to classify subjects in a population for the detection of colon cell proliferative disorders.

13 Claims, 13 Drawing Sheets

(56) References Cited

U.S. PATENT DOCUMENTS

| | | | |
|---|---|---|---|
| 8,168,385 B2 | 5/2012 | Brenner | |
| 8,318,433 B2 | 11/2012 | Brenner | |
| 9,040,239 B1 | 5/2015 | Zheng et al. | |
| 9,080,210 B2 | 7/2015 | Van Eijk et al. | |
| 9,128,101 B2 * | 9/2015 | Halbert | A61P 15/04 |
| 9,447,452 B2 | 9/2016 | Rao et al. | |
| 10,337,053 B2 | 7/2019 | Rao et al. | |
| 10,443,091 B2 | 10/2019 | Rao et al. | |
| 10,533,213 B2 | 1/2020 | Rao et al. | |
| 10,731,204 B2 | 8/2020 | Rao et al. | |
| 10,767,216 B2 | 9/2020 | Rao et al. | |
| 10,774,373 B2 | 9/2020 | Rao et al. | |
| 10,978,175 B2 | 4/2021 | Van Eijk et al. | |
| 11,072,818 B2 | 7/2021 | Rao et al. | |
| 11,208,683 B2 | 12/2021 | Rao et al. | |
| 11,472,885 B2 * | 10/2022 | DeFalco | A61K 39/3955 |
| 11,514,289 B1 | 11/2022 | Otte et al. | |
| 11,681,953 B2 | 6/2023 | Drake et al. | |
| 11,781,959 B2 | 10/2023 | Delubac | |
| 2010/0131286 A1 | 5/2010 | Houlgatte et al. | |
| 2010/0151471 A1 | 6/2010 | Faham et al. | |
| 2013/0072400 A1 | 3/2013 | Casal Álvarez et al. | |
| 2014/0365243 A1 | 12/2014 | Varadan et al. | |
| 2015/0226744 A1 | 8/2015 | Weinhausel et al. | |
| 2017/0277844 A1 | 9/2017 | Apte et al. | |
| 2018/0102187 A1 | 4/2018 | Apte et al. | |
| 2018/0119137 A1 | 5/2018 | Matsuguchi et al. | |
| 2019/0204324 A1 | 7/2019 | Cho et al. | |
| 2020/0005901 A1 * | 1/2020 | Cohen | G16H 50/30 |
| 2020/0116722 A1 | 4/2020 | Gray et al. | |
| 2020/0232894 A1 | 7/2020 | Delubac | |
| 2021/0010076 A1 | 1/2021 | Delubac et al. | |
| 2021/0057046 A1 | 2/2021 | Liu et al. | |
| 2021/0174958 A1 | 6/2021 | Drake et al. | |
| 2021/0210205 A1 | 7/2021 | Drake et al. | |
| 2021/0230684 A1 | 7/2021 | Ariazi et al. | |
| 2021/0272653 A1 | 9/2021 | Ulz et al. | |
| 2024/0058446 A1 * | 2/2024 | Corey | A61K 39/464429 |

FOREIGN PATENT DOCUMENTS

| | | |
|---|---|---|
| GB | 2494741 A | 3/2013 |
| WO | WO-2016119190 A1 | 8/2016 |
| WO | WO-2019060716 A1 | 3/2019 |
| WO | WO-2019100024 A1 | 5/2019 |
| WO | WO-2019147663 A1 | 8/2019 |
| WO | WO-2019191649 A1 | 10/2019 |
| WO | WO-2019195268 A2 | 10/2019 |
| WO | WO-2019200410 A1 | 10/2019 |
| WO | WO-2020076772 A1 | 4/2020 |
| WO | WO-2020243609 A1 | 12/2020 |
| WO | WO-2021202351 A1 | 10/2021 |
| WO | WO-2021222220 A2 | 11/2021 |
| WO | WO-2022076237 A1 | 4/2022 |
| WO | WO-2022140116 A1 | 6/2022 |
| WO | WO-2022204358 A1 | 9/2022 |
| WO | WO-2022261192 A1 | 12/2022 |
| WO | WO-2023003851 A1 | 1/2023 |
| WO | WO-2023147472 A1 | 8/2023 |
| WO | WO-2023183468 A2 | 9/2023 |
| WO | WO-2023235878 A2 | 12/2023 |
| WO | WO-2023244983 A1 | 12/2023 |
| WO | WO-2023250441 A2 | 12/2023 |

OTHER PUBLICATIONS

Booth et al. Quantitative Sequencing of 5-Methylcytosine and 5-Hydroxymethylcytosine at Single-Base Resolution. Science 336(6083):934-937 (2012).

Friedland et al.: Development and Clinical Validation of a blood test for early detection of colorectal adenomas and cancer. Abstract 32305, Poster ASCO GI Meeting [1-1] (2021).

Frommer et al. A genomic sequencing protocol that yields a positive display of 5-methylcytosine residues in individual DNA strands. PNAS USA 89:1827-1831 (1992).

Golub et al. Molecular classification of cancer: Class discovery and class prediction by gene expression monitoring, Science, American Association for the Advancement of Science, 286:5439 (Oct. 15, 1999).

Herman, J.G., et al., "Methylation-Specific PCR: A Novel PCR Assay for Methylation Status of CpG Islands." Proceedings of the National Academy of Science USA 93:9821-9826, Sep. 1996.

Kourou et al. Machine learning applications in cancer prognosis and prediction. Comput Struct Biotechnol J.13:8-17 (2014).

Liu et al.: An individualized predictor of health and disease using paired reference and target samples. BMC Bioinformatics 17:47 [1-15] (2016).

Liu et al. Bisulfite-Free Direct Detection of 5-Methylcytosine and 5-Hydroxymethylcytosine at Base Resolution. Nature Biotechnology 37(4):424-429 (2019).

Manghnani et al.: METCC: METric learning for Confounder Control Making distance matter in high dimensional biological analysis. arXiv: 1812.03188v1 [cs.LG] [1-10] (2018).

Negm et al.: Human Blood Autoantibodies in the Detection of Colorectal Cancer. PLoS One 11(7):e0156971, pp. 1-14 doi:10.1371/journal.pone.0156971 (2016).

Schutsky et al. Nondestructive, Base-Resolution Sequencing of 5-Hydroxymethylcytosine Using a DNA Deaminase. Nature Biotechnology 36(11):1083-1090 (2018).

Singh, et al. "Gene expression correlates of clinical prostate cancer behavior." Cancer Cell. vol. 1, pp. 203-209 (2002).

Wan et al.: Machine learning enables detection of early-stage colorectal cancer by whole-genome sequencing of plasma cell-free DNA. bioRxiv prePrint URL:https://doi.org/10.1101/478065 [1-22] (2018).

Yu et al.: Tet-assisted bisulfite sequencing of 5-hydroxymethylcytosine. Nat Protoc. 7(12):2159-2170 doi:10.1038/nprot.2012.137 (2012).

Zhang et al. Tet-mediated covalent labelling of 5-methylcytosine for its genome-wide detection and sequencing, Nat Commun. 2013;4:1517.

EP20210878257.1 Partial European Search Report dated Nov. 25, 2024.

Negm, Ola H., et al. Human blood autoantibodies in the detection of colorectal cancer. PLoS One 11(7): e0156971. (2016), 14 pages.

PCT/US2021/052816 International Preliminary Report on Patentability dated Apr. 20, 2023.

PCT/US2021/052816 International Search Report and Written Opinion dated Feb. 14, 2022.

PCT/US2021/052816 Invitation to Pay Additional Fees dated Dec. 8, 2021.

* cited by examiner

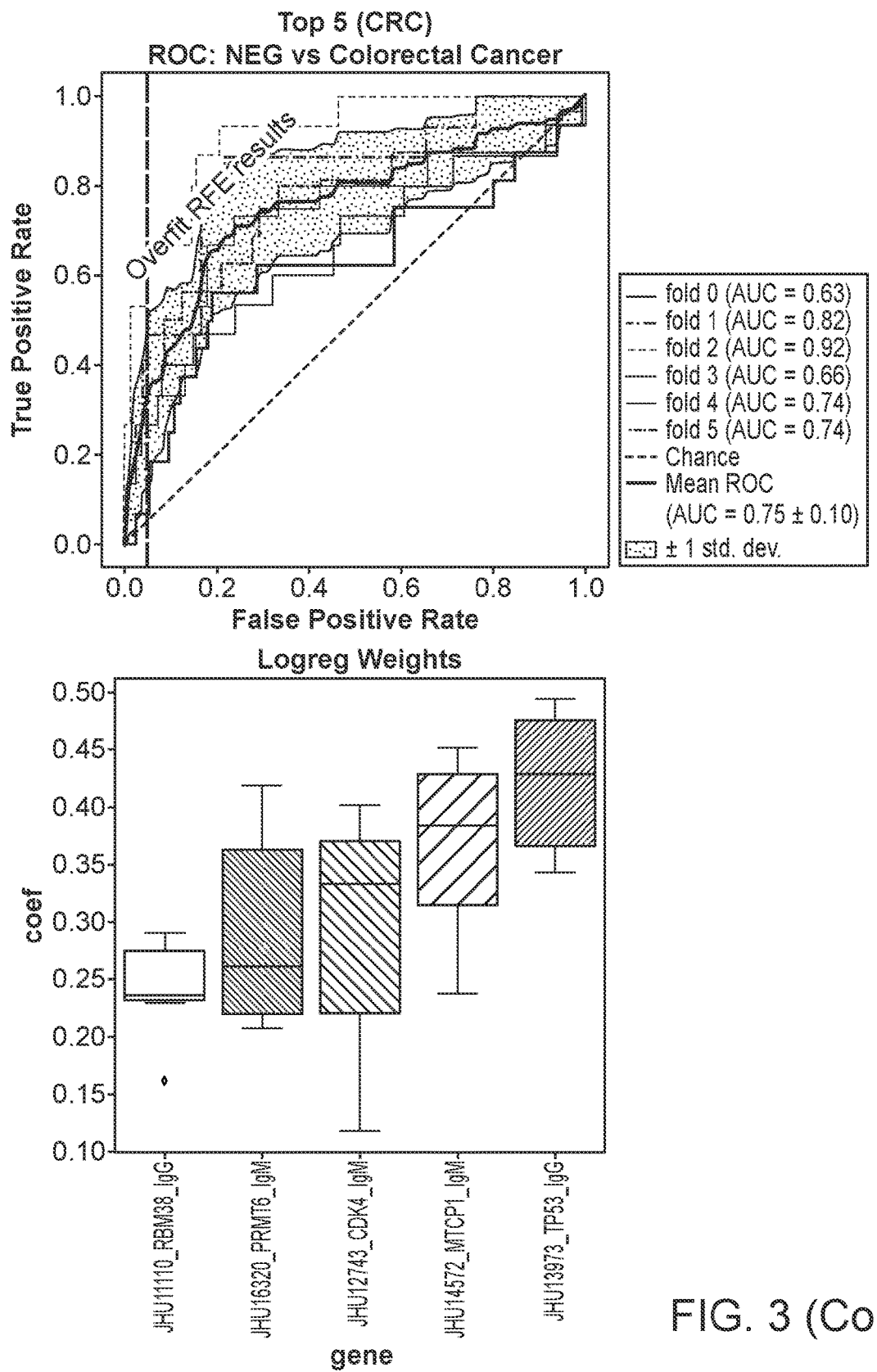
FIG. 3 (Cont. 1)

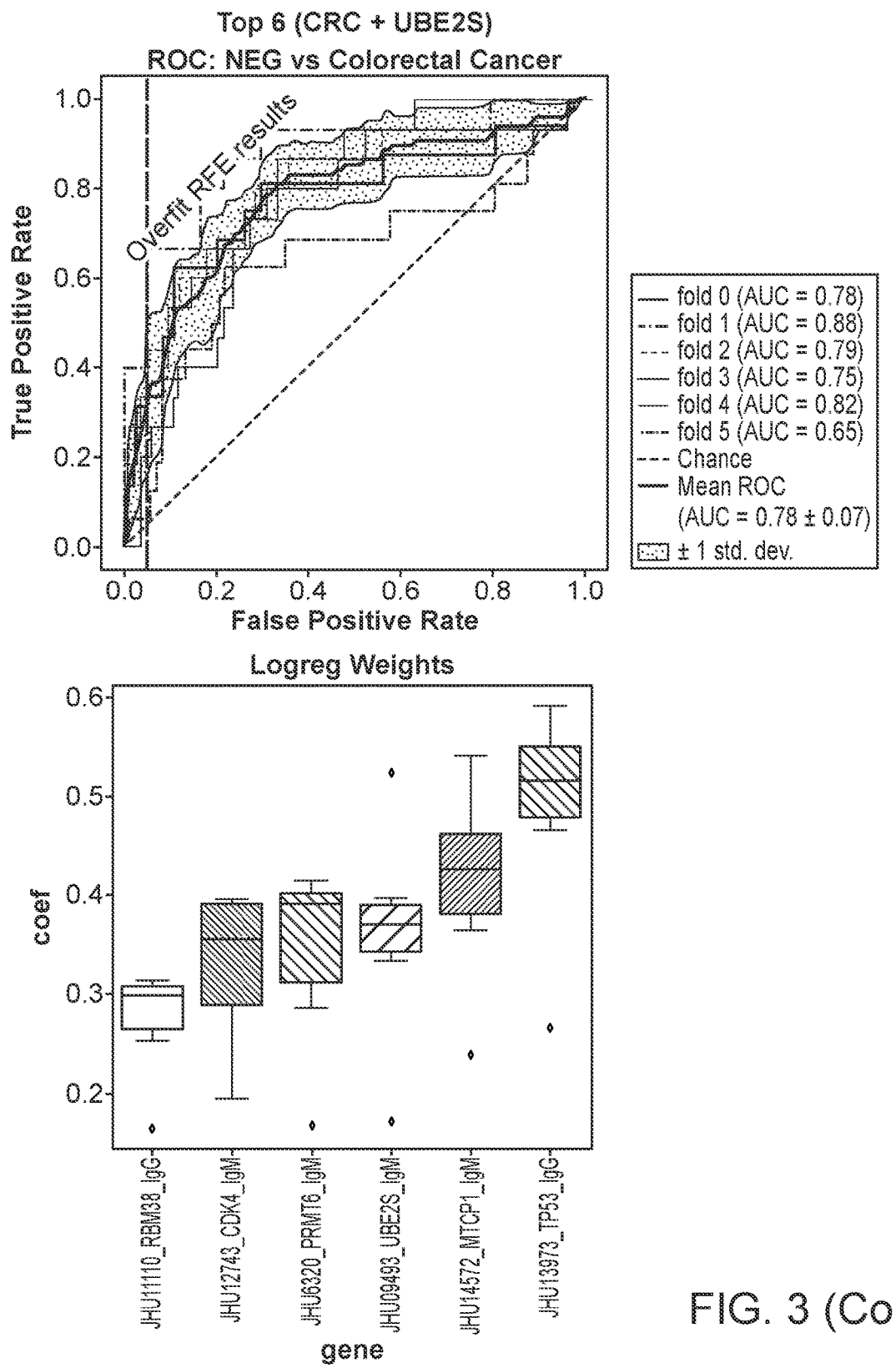
FIG. 3 (Cont. 2)

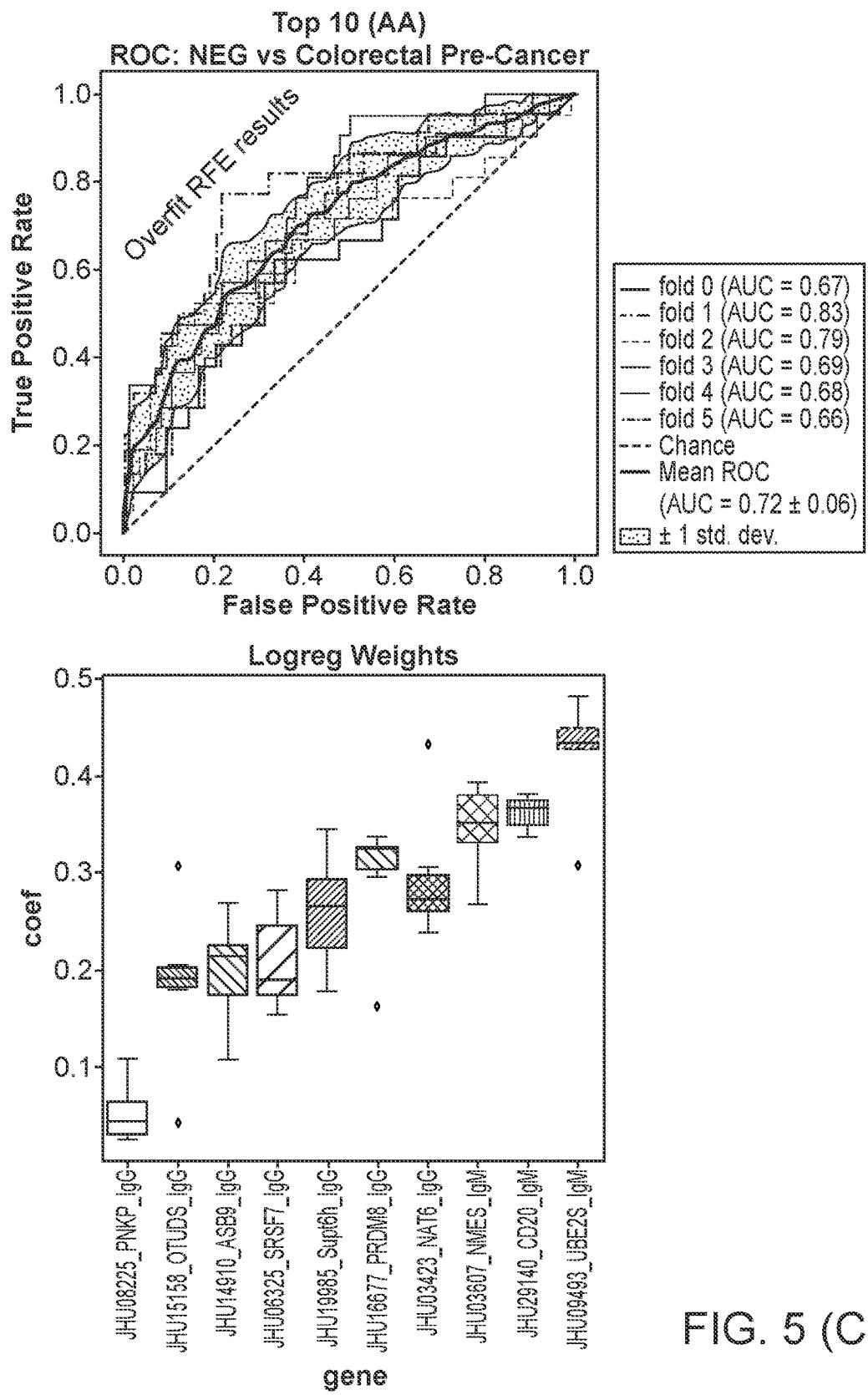
FIG. 5 (Cont. 1)

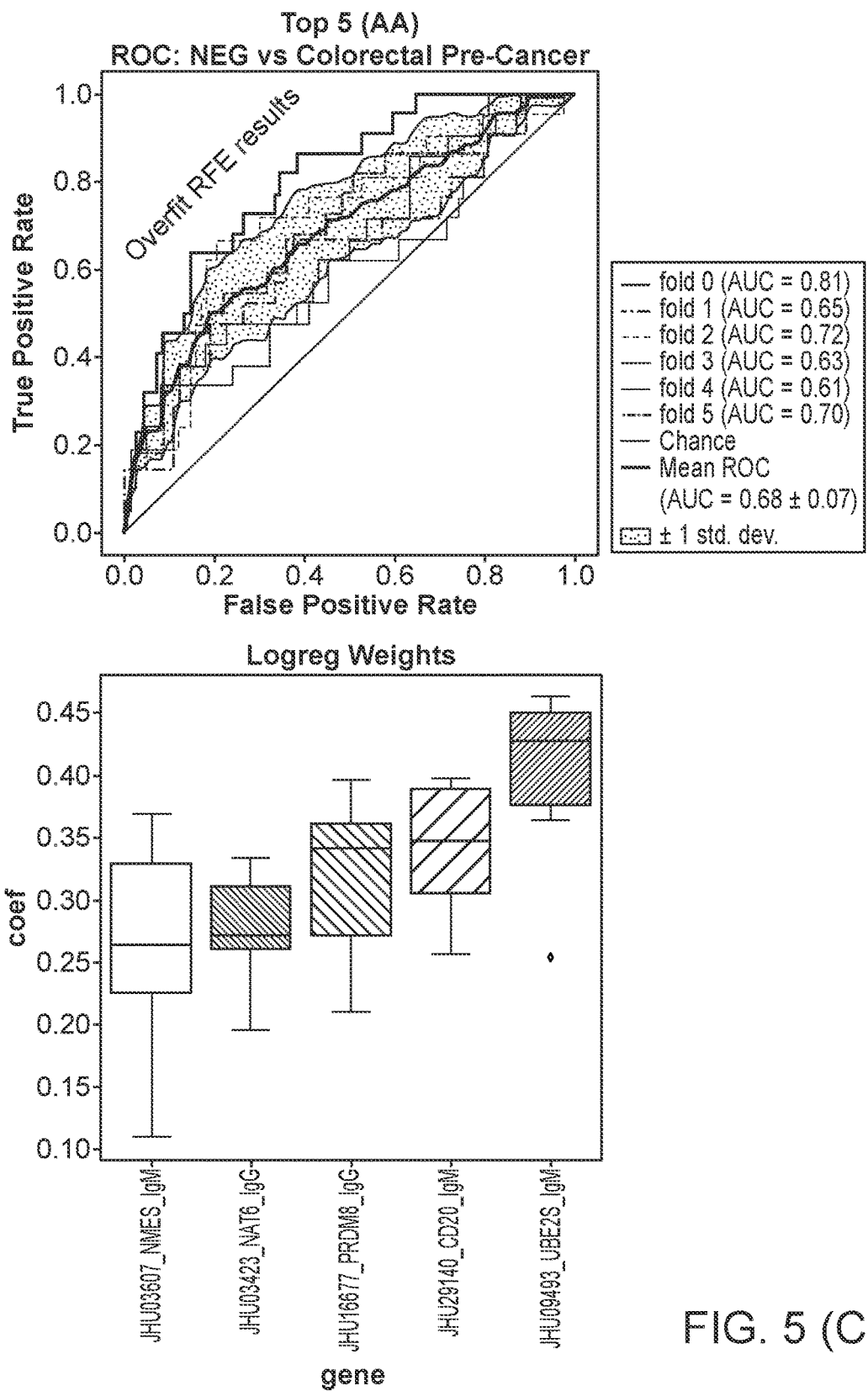
FIG. 5 (Cont. 2)

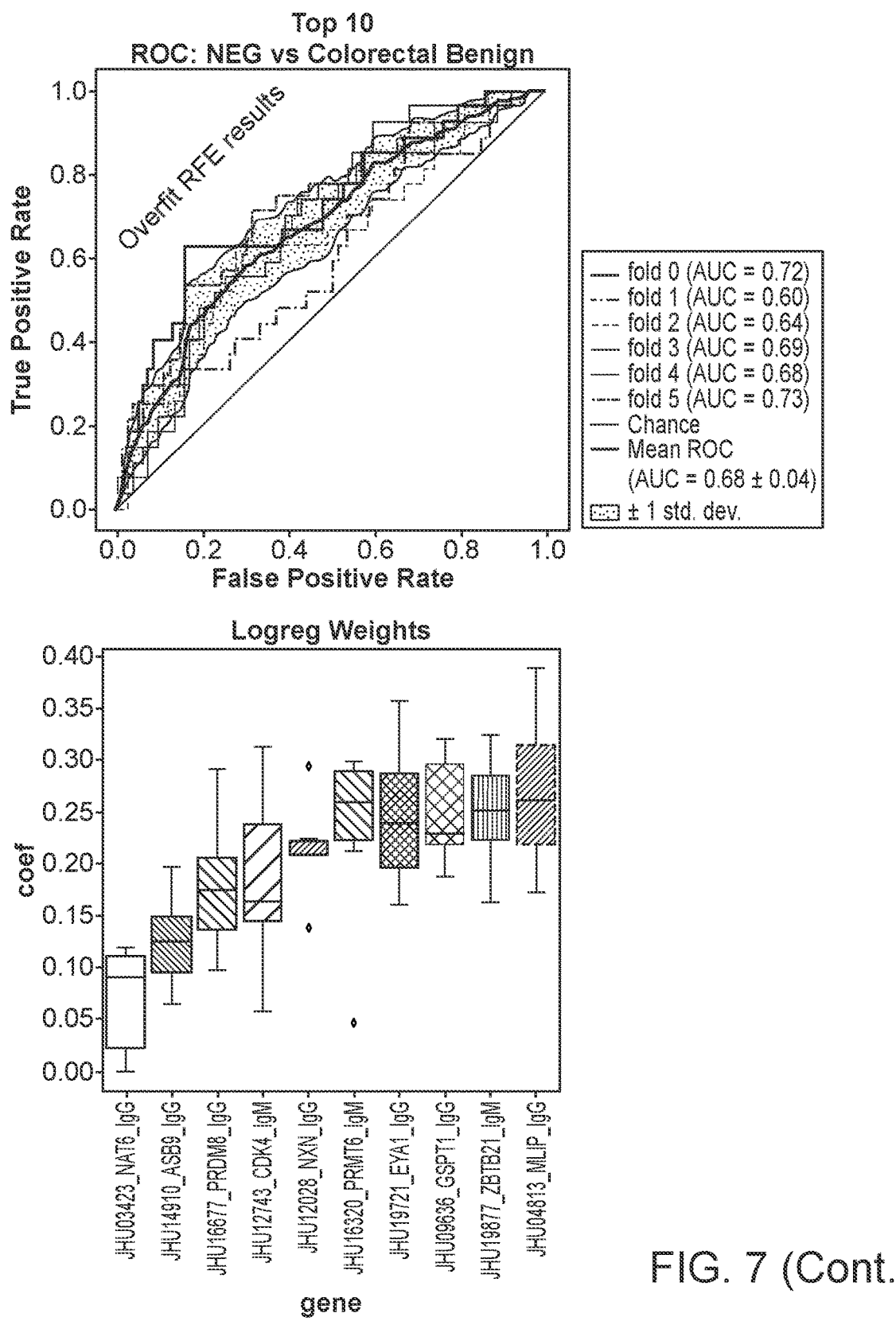
FIG. 7 (Cont. 1)

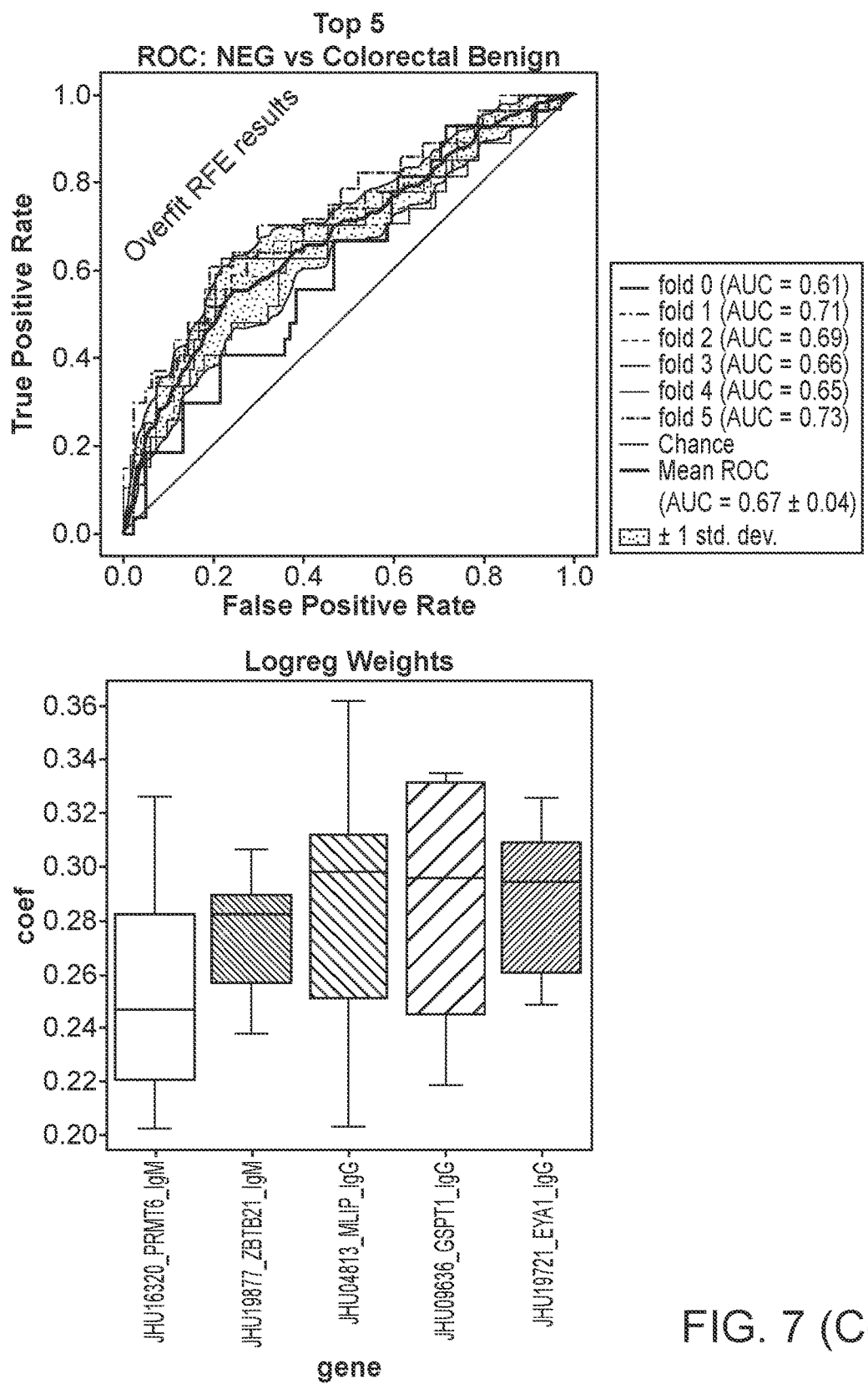
FIG. 7 (Cont. 2)

MARKERS FOR THE EARLY DETECTION OF COLON CELL PROLIFERATIVE DISORDERS

CROSS-REFERENCE TO RELATED APPLICATIONS

This application is a continuation of International Patent Application No. PCT/US2021/052816, filed Sep. 30, 2021, which claims the benefit of U.S. Provisional Patent Application No. 63/087,728, filed Oct. 5, 2020, each of which is incorporated by reference herein in its entirety.

FIELD

This disclosure is related to biomarkers and methods for the early identification of colon cell proliferative disorders including advanced adenoma and colorectal cancer.

BACKGROUND

Colorectal cancer is the leading cause of cancer related mortality in the western world. Although colorectal cancer is one of the best characterized solid tumors, colorectal cancer continues to be one of the main causes of death in developed countries because of late diagnosis. Among other reasons, late diagnosis of patients is due to the fact that diagnostic tests, such as colonoscopy, are performed too late. Deaths from colorectal cancer can be prevented through effective screening.

SUMMARY

The present disclosure provides methods and systems directed to autoantibody profiling of biological samples associated with colorectal cancer detection and disease progression.

In an aspect, the present disclosure provides a predetermined autoantibody panel characteristic of a colon cell proliferative disorder comprising autoantibodies to 3 or more antigens selected from the group consisting of NME5, USP16, UBE2S, RNF41, CD20, ANKHD1, TXNL1, NAT6, Supt6h, PRDM8, OTUD5, PNKP, SRSF7, ASB9, NXN, ZBTB21, EYA1, GSPT1, MLIP, RBM38, ARMC5, TP53, BRD9, CDK4, PRMT6, PCOLCE, and SDCBP.

In some embodiments, the 3 or more autoantibodies are IgG autoantibodies, IgM autoantibodies, or a combination thereof.

In some embodiments, the panel is configured to distinguish healthy subjects, subjects with benign colon polyp, subjects with advanced adenoma, or subjects with colorectal cancer.

In some embodiments, the panel is configured to indicate advanced adenoma and comprises: 1) IgM autoantibodies to at least 3 antigens selected from the group consisting of NME5, USP16, UBE2S, RNF41, CD20, and SDCBP; 2) IgM autoantibodies to at least one antigen selected from the group consisting of UBE2S, NME5, and CD20; 3) IgG autoantibodies to at least 3 antigens selected from the group consisting of ANKHD1, TXNL1, NAT6, Supt6h, PRDM8, OTUD5, PNKP, SRSF7, PCOLCE, and ASB9; 4) IgG autoantibodies to at least one antigen selected from the group consisting of ASB9, NAT6, Supt6h, and PRDM8; or a combination thereof.

In some embodiments, the panel is configured to indicate colorectal cancer and comprises: 1) IgM autoantibodies to at least 3 antigens selected from the group consisting of PELO, CDK4, MTP1, PRMT6 ZBTB2, and PCOLCE; 2) IgM autoantibodies to at least one antigen selected from the group consisting of CDK4, MTCP1, and PCOLCE; 3) IgG autoantibodies to at least 3 antigens selected from the group consisting of TSSC4, BRD9, BCCIP, and TP53; 4) IgG autoantibodies to TP53; or a combination thereof.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumor, gastrointestinal carcinoid tumor, gastrointestinal stromal tumor (GIST), lymphoma, and sarcoma.

In another aspect, the present disclosure provides a classifier configured to distinguish a population of healthy subjects from subjects with a colon cell proliferative disorder, comprising: sets of measured values representative of autoantibodies from a predetermined autoantibody panel characteristic of the colon cell proliferative disorder, wherein the measured values are obtained from autoantibody expression data from healthy subjects and subjects having the colon cell proliferative disorder, wherein the measured values are used to generate a set of features corresponding to properties of the autoantibodies, wherein the set of features are inputted to a machine learning or statistical model, wherein the model provides a feature vector useful as the classifier capable of distinguishing the population of healthy subjects from subjects having the colon cell proliferative disorder.

In some embodiments, the predetermined autoantibody panel comprises autoantibodies to 3 or more antigens selected from the group consisting of NME5, USP16, UBE2S, RNF41, CD20, ANKHD1, TXNL1, NAT6, Supt6h, PRDM8, OTUD5, PNKP, SRSF7, ASB9, PRDM8, NXN, ZBTB21, EYA1, GSPT1, MLIP, RBM38, ARMC5, TP53, BRD9, CDK4, PRMT6, PCOLCE, and SDCBP.

In some embodiments, the 3 or more autoantibodies are IgG autoantibodies, IgM autoantibodies, or a combination thereof.

In some embodiments, the panel is configured to distinguish healthy subjects, subjects with benign colon polyp, subjects with advanced adenoma, or subjects with colorectal cancer.

In some embodiments, the panel is configured to indicate advanced adenoma and comprises: 1) IgM autoantibodies to at least 3 antigens selected from the group consisting of NME5, USP16, UBE2S, RNF41, CD20, and SDCBP; 2) IgM autoantibodies to at least one antigen selected from the group consisting of UBE2S, NME5, and CD20; 3) IgG autoantibodies to at least 3 antigens selected from the group consisting of ANKHD1, TXNL1, NAT6, Supt6h, PRDM8, OTUD5, PNKP, SRSF7, PCOLCE, and ASB9; 4) IgG autoantibodies to at least one antigen selected from the group consisting of ASB9, NAT6, Supt6h, and PRDM8; or a combination thereof.

In some embodiments, the panel is configured to indicate colorectal cancer and comprises: 1) IgM autoantibodies to at least 3 antigens selected from the group consisting of PELO, CDK4, MTP1, PRMT6 ZBTB2, and PCOLCE; 2) IgM autoantibodies to at least one antigen selected from the group consisting of CDK4, MTCP1, and PCOLCE; 3) IgG autoantibodies to at least 3 antigens selected from the group consisting of TSSC4, BRD9, BCCIP, and TP53; 4) IgG autoantibodies to TP53; or a combination thereof.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumor, gastrointestinal carcinoid tumor, gastrointestinal stromal tumor (GIST), lymphoma, and sarcoma.

In another aspect, the present disclosure provides a system comprising a machine learning model classifier for detecting a colon cell proliferative disorder comprising a computer-readable medium comprising a classifier operable to classify the subjects based at least in part on a predetermined autoantibody panel; and one or more processors for executing instructions stored on the computer-readable medium.

In some embodiments, the classifier is loaded into a memory of a computer system, wherein the machine learning model is trained using training vectors obtained from training biological samples, wherein a first subset of the training biological samples identified as having a colon cell proliferative disorder, and wherein a second subset of the training biological samples identified as not having a colon cell proliferative disorder.

In some embodiments, the predetermined autoantibody panel comprises autoantibodies to 3 or more antigens selected from the group consisting of NME5, USP16, UBE2S, RNF41, CD20, ANKHD1, TXNL1, NAT6, Supt6h, PRDM8, OTUD5, PNKP, SRSF7, ASB9, PRDM8, NXN, ZBTB21, EYA1, GSPT1, MLIP, RBM38, ARMC5, TP53, BRD9, CDK4, PRMT6, PCOLCE, and SDCBP.

In some embodiments, the classifier is selected from the group consisting of a deep learning classifier, a neural network classifier, a linear discriminant analysis (LDA) classifier, a quadratic discriminant analysis (QDA) classifier, a support vector machine (SVM) classifier, a random forest (RF) classifier, K nearest neighbor classifier, a linear kernel support vector machine classifier, a first or second order polynomial kernel support vector machine classifier, a ridge regression classifier, an elastic net algorithm classifier, a sequential minimal optimization algorithm classifier, a naïve Bayes algorithm classifier, and principal component analysis classifier.

In another aspect, the present disclosure provides a method for determining an autoantibody profile of a subject, comprising: obtaining a biological sample from a subject; and measuring an amount of an autoantibody from a predetermined panel of autoantibodies comprising autoantibodies to 3 or more antigens selected from the group consisting of NME5, USP16, UBE2S, RNF41, CD20, ANKHD1, TXNL1, NAT6, Supt6h, PRDM8, OTUD5, PNKP, SRSF7, ASB9, NXN, ZBTB21, EYA1, GSPT1, MLIP, RBM38, ARMC5, TP53, BRD9, CDK4, PRMT6, PCOLCE, and SDCBP, to provide the autoantibody profile of the subject.

In some embodiments, the autoantibody profile is associated with a colon cell proliferative disorder and provides classification of the subject as having the colon cell proliferative disorder.

In some embodiments, the biological sample obtained from the subject is selected from the group consisting of body fluids, stool, colonic effluent, urine, blood plasma, blood serum, whole blood, isolated blood cells, cells isolated from the blood, tissue biopsy, and combinations thereof.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumor, gastrointestinal carcinoid tumor, gastrointestinal stromal tumor (GIST), lymphoma, and sarcoma.

In another aspect, the present disclosure provides a method for detecting a colon cell proliferative disorder in a subject, comprising: obtaining a biological sample from the subject; measuring an amount of an autoantibody from a predetermined autoantibody panel comprising autoantibodies to 3 or more antigens selected from the group consisting of NME5, USP16, UBE2S, RNF41, CD20, ANKHD1, TXNL1, NAT6, Supt6h, PRDM8, OTUD5, PNKP, SRSF7, ASB9, NXN, ZBTB21, EYA1, GSPT1, MLIP, RBM38, ARMC5, TP53, BRD9, CDK4, PRMT6, PCOLCE, and SDCBP, to provide an autoantibody profile of the subject; and processing the autoantibody profile using a machine learning model trained to be capable of distinguishing between healthy subjects and subjects with the colon cell proliferative disorder to determine an output value associated with presence of the colon cell proliferative disorder, thereby indicating the presence of the colon cell proliferative disorder in the subject.

In some embodiments, the autoantibody profile is associated with a colon cell proliferative disorder and provides classification of the subject as having the colon cell proliferative disorder.

In some embodiments, the method further comprises detecting a methylation status of nucleic acid molecules in the biological sample to provide a methylation profile.

In some embodiments, the method further comprises processing the methylation profile using the machine learning model, wherein the methylation profile is combined with the autoantibody profile in the machine learning model to distinguish between healthy subjects and subjects with the colon cell proliferative disorder.

In some embodiments, the method further comprises measuring an amount of one or more proteins in the biological sample to provide a protein profile.

In some embodiments, the method further comprises processing the protein profile using the machine learning model, wherein the protein profile is combined with the autoantibody profile in the machine learning model to distinguish between healthy subjects and subjects with the colon cell proliferative disorder.

In some embodiments, the biological sample obtained from the subject is selected from the group consisting of body fluids, stool, colonic effluent, urine, blood plasma, blood serum, whole blood, isolated blood cells, cells isolated from the blood, tissue biopsy, and combinations thereof.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumor, gastrointestinal carcinoid tumor, gastrointestinal stromal tumor (GIST), lymphoma, and sarcoma.

In some embodiments, the panel is configured to indicate advanced adenoma and comprises: 1) IgM autoantibodies to at least 3 antigens selected from the group consisting of NME5, USP16, UBE2S, RNF41, CD20, and SDCBP; 2) IgM autoantibodies to at least one antigen selected from the group consisting of UBE2S, NME5, and CD20; 3) IgG autoantibodies to at least 3 antigens selected from the group consisting of ANKHD1, TXNL1, NAT6, Supt6h, PRDM8, OTUD5, PNKP, SRSF7, PCOLCE, and ASB9; 4) IgG autoantibodies to at least one antigen selected from the group consisting of ASB9, NAT6, Supt6h, and PRDM8; or a combination thereof.

In some embodiments, the panel is configured to indicate colorectal cancer and comprises: 1) IgM autoantibodies to at least 3 antigens selected from the group consisting of PELO, CDK4, MTP1, PRMT6 ZBTB2, and PCOLCE; 2) IgM autoantibodies to at least one antigen selected from the group consisting of CDK4, MTCP1, and PCOLCE; 3) IgG autoantibodies to at least 3 antigens selected from the group consisting of TSSC4, BRD9, BCCIP, and TP53; 4) IgG autoantibodies to TP53; or a combination thereof.

In some embodiments, the method further comprises administering a treatment for the colon cell proliferative disorder in the subject. In some embodiments, the treatment is selected from the group consisting of surgery, radiofrequency ablation, chemotherapy, radiation therapy, targeted therapy, and immune therapy.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent that publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
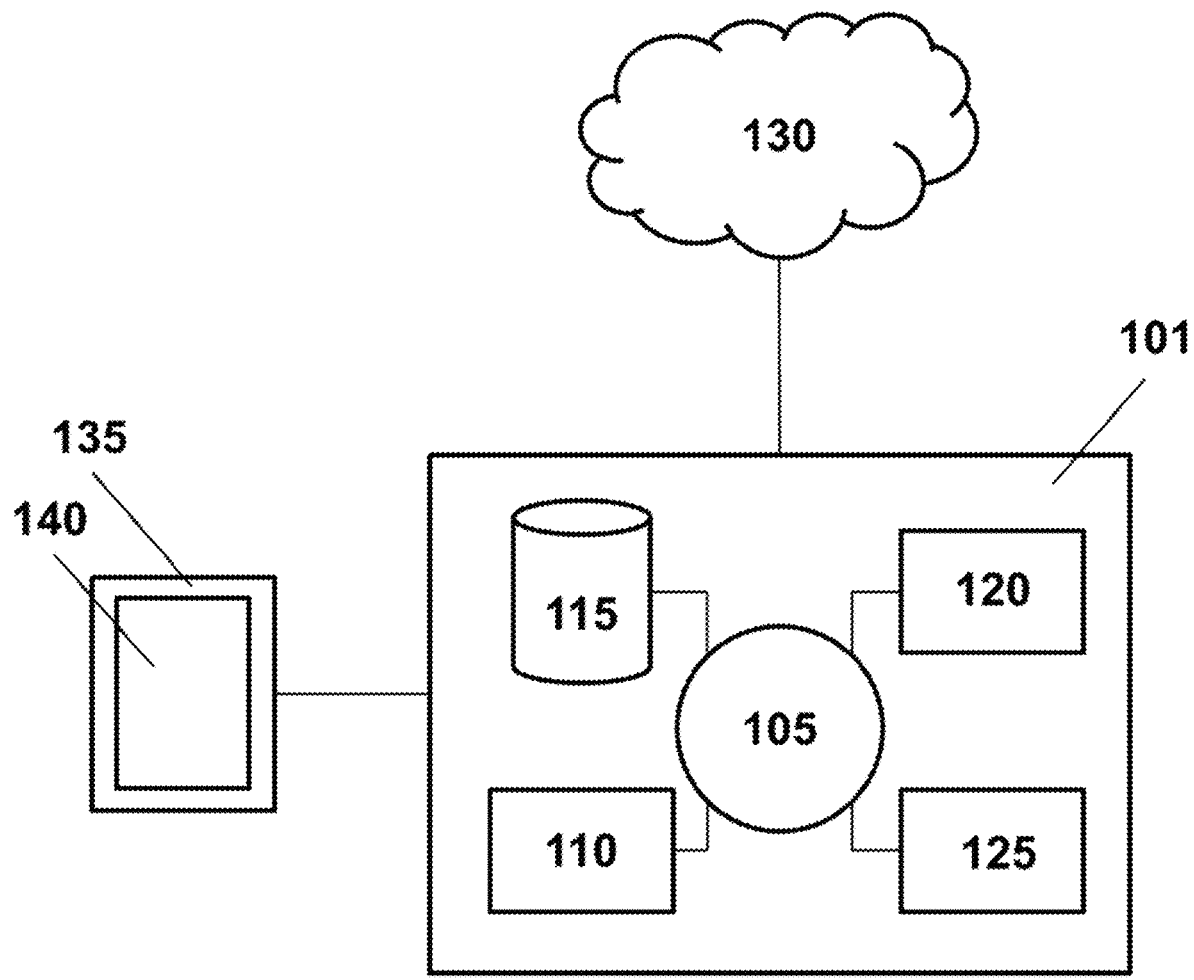
FIG. 1 provides a schematic of a computer system that is programmed or otherwise configured with the machine learning models and classifiers in order to implement methods provided herein.

While various embodiments of the invention have been shown and described herein, it will be obvious to those having ordinary skill in the art that such embodiments are provided by way of example only. Numerous variations, changes, and substitutions can occur to those having ordinary skill in the art without departing from the invention. It should be understood that various alternatives to the embodiments of the invention described herein can be employed.

Colorectal cancer is the leading cause of cancer related mortality in the western world. Although colorectal cancer is one of the best characterized solid tumors, colorectal cancer continues to be one of the main causes of death in developed countries because of late diagnosis. Among other reasons, late diagnosis of patient is due to the fact that diagnostic tests, such as colonoscopy, are performed too late. Deaths from colorectal cancer can be prevented through effective screening. Specific antibody responses to tumor related antigens have been identified in patients with cancer. Because these antibody responses can be triggered by changes in the structure or expression of self-proteins in tumor cells, the presence of some antibodies may serve as potential immunological markers of cancer.

The present disclosure relates generally to cancer detection and disease monitoring. More particularly, the present disclosure relates to cancer-related autoantibody detection and disease monitoring in colon cell proliferative disorders such as early-stage colorectal cancer. Specifically, circulating autoantibody signature panels and uses thereof are provided for identifying human subjects having, or at risk of developing, colon cell proliferative disorders such as colorectal cancer (CRC) and/or colorectal adenomas (CA), for example, advanced colorectal adenomas (AA).

The present disclosure describes tumor antigen-associated autoantibodies ("tAAbs" or "autoantibodies") in a subject that are indicative of the presence of a colon cell proliferative disorder, or a high risk of developing a colon cell proliferative disorder, for example, when the subject has a colorectal lesion. Cancer screening and monitoring improve survival outcomes because early detection allows for elimination of the cancer before its growth and spread. In colorectal cancer, for instance, colonoscopies play a role in improving early diagnosis. Unfortunately, patient compliance rates are low, and screening is conducted below recommended regularity due to the invasiveness of the procedure.

Described herein are methods for screening or identifying subjects having, or at risk of having, a colon cell proliferative disorder based at least in part on an expression profile or abundance of autoantibodies that are up-regulated or over-expressed in subjects suffering from colon cell proliferative disorders. Further described herein are methods for obtaining data useful for diagnosis of a colon cell proliferative disorder in a subject, for example, a human subject.

A colon cell proliferative disorder may be of any tumor stage (e.g., TX, T0, Tis, T1, T2, T3, T4); any regional lymph node or distant metastasis stage (e.g., NX, N0, N1, M0, M1); any stage (e.g., Stage 0 (Tis, NO, M0), Stage IA (T1, NO, M0), Stage IIA (T3, NO, M0), Stage IIB (T1-3, N1, M0), Stage III (T4, Any N, M0), or Stage IV (Any T, Any N, M1)); resectable; locally advanced (unresectable); or metastatic.

Screening tools may be compromised due to false positive and false negative results, and specificity and sensitivity. An ideal cancer screening tool may have a high Positive Predictive Value (PPV), which minimizes unnecessary investigations (low false positives) but detects a vast majority of cancers (low false negative). Another key compromise is "detection sensitivity", which is distinct from test sensitivity. Detection sensitivity is the lower limit of detecting a tumor based on size. Allowing a tumor to grow to a size large enough to release circulating tumor markers at detectable levels defeats the purpose of early detection and prevention of cancer progression. Hence, there is a need for highly sensitive and effective blood-based screens for early diagnosis of colorectal cancer.

The detection of circulating tumor DNA, known as a "liquid biopsy," allows for the detection and informative investigation of tumors in a non-invasive manner. Identification of tumor specific mutations in these liquid biopsies have been used to diagnose colon, breast, and prostate cancers. However, due to the high background of normal (i.e., non-tumor-derived) DNA present in circulation, these techniques may be limited in sensitivity. Thus, there remains a need for more sensitive and specific screening tools for detecting early-stage or low tumor-burden colorectal cancer tumor markers for relapse screening and primary screening of at-risk populations. Circulating autoantibodies to tumor-associated antigens provide a source of informative biomarkers in the liquid biopsy sample that may be used in the machine learning models described herein.

The present disclosure provides methods and systems directed to profiling circulating autoantibodies associated with a colon cell proliferative disorder and progression thereof, for example, a colorectal cancer. Those autoantibodies that are indicative of the presence of a colon cell proliferative disorder or a high risk of developing the colon cell proliferative disorder may be used for diagnosing, treating, or preventing progression of a colon cell proliferative disorders as early as possible, for example, when a subject only has a colorectal lesion. Further provided herein are kits and methods for diagnosing colon cell proliferative disorders or assessing the risk of developing colon cell proliferative disorders in a subject, particularly, when the subject has a colorectal lesion.

In an aspect, provided herein are methods of using a panel of autoantibodies for distinguishing samples from subjects based on a disease status. In other aspects, provided herein are methods, assays, and kits directed to detecting, differentiating, and distinguishing a colon cell proliferative disorder using a panel of autoantibodies. Non-limiting examples of colon cell proliferative disorder include adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas.

In some embodiments, provided herein are methods of using one or more autoantibodies selected as markers for the differentiation, detection, and distinguishing of a colon cell proliferative disorder.

Definitions

As used in the specification and claims, the singular form "a", "an", and "the" include plural references unless the context clearly dictates otherwise. For example, the term "a nucleic acid" includes a plurality of nucleic acids, including mixtures thereof.

As used herein, the term "subject" refers to an entity or a medium that has testable or detectable genetic information. A subject can be a person, individual, or patient. A subject can be a vertebrate, such as, for example, a mammal. Non-limiting examples of mammals include humans, simians, farm animals, sport animals, rodents, and pets. The subject may be displaying a symptom(s) indicative of a health or physiological state or condition of the subject, such as a disease or disorder of the subject. As an alternative, the subject can be asymptomatic with respect to such health or physiological state or condition.

As used herein, the term "sample" generally refers to a biological sample obtained from or derived from one or more subjects. Biological samples may be cell-free biological samples or substantially cell-free biological samples, or may be processed or fractionated to produce cell-free biological samples. For example, cell-free biological samples may include cell-free ribonucleic acid (cfRNA), cell-free deoxyribonucleic acid (cfDNA), cell-free fetal DNA (cffDNA), proteins, autoantibodies, plasma, serum, urine, saliva, amniotic fluid, and derivatives thereof. Cell-free biological samples may be obtained or derived from subjects using an ethylenediaminetetraacetic acid (EDTA) collection tube, a cell-free RNA collection tube (e.g., Streck® RNA Complete BCT®), or a cell-free DNA collection tube (e.g., Streck® Cell-Free DNA BCT®). Cell-free biological samples may be derived from whole blood samples by fractionation (e.g., by differential centrifugation). Biological samples or derivatives thereof may contain cells. For example, a biological sample may be a blood sample or a derivative thereof (e.g., blood collected by a collection tube or blood drops).

As used herein, the term "cell-free sample" generally refers to a biological sample that is substantially devoid of intact cells. A cell-free sample may be derived from a biological sample that is itself substantially devoid of cells or may be derived from a sample from which cells have been removed. Non-limiting examples of cell-free samples include those derived from blood, serum, plasma, urine, semen, sputum, feces, ductal exudate, lymph, and recovered lavage.

As used herein, the term "colon cell proliferative disorder" generally refers to a disorder or disease that comprises disordered or aberrant proliferation of cells in the colon or rectum. Non-limiting examples of colon cell proliferative disorders include adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas. As used herein, the abbreviation "CRC" is used to identify biological samples from a subject diagnosed with colorectal cancer. As used herein, the abbreviation "AA" is used to identify samples from a subject diagnosed with at least one advanced adenoma. As used herein, the abbreviation "NAA" is used to identify samples from a subject diagnosed with a colorectal tumor that is benign and not an advanced adenoma or colorectal cancer.

As used herein, the term "colorectal cancer" is a medical condition generally characterized by cancer of cells of the intestinal tract below the small intestine (i.e., the large intestine (colon), for example, the cecum, ascending colon, transverse colon, descending colon, sigmoid colon, and rectum).

As used herein, the term "colorectal adenoma" generally refers to adenomas of the colon, also called adenomatous polyps, which is a benign and pre-cancerous stage of the colorectal cancer. Colorectal adenomas may be indicative of a high risk of progression to colorectal cancer.

As used herein, the term "advanced colorectal adenoma" refers to adenomas having a size of at least 10 mm or histologically having high grade dysplasia or a villous component higher than 20%.

As used herein, the term "at risk of developing a colon cell proliferative disorder" or "high risk of developing a colon cell proliferative disorder" generally refers to a subject having an increased risk of developing a colon cell proliferative disorder in the near future as compared to a subject not having the colon cell proliferative disorder or having a low risk of developing the colon cell proliferative disorder in the near future. As used herein, the term "near future" generally refers to a duration of about 1 month to about 2 years, about 6 months to about 18 months, or about 1 year.

As used herein, the terms cancer "type" and "subtype" generally are used relatively herein, such that one "type" of cancer, such as breast cancer, may be "subtypes" based on, e.g., stage, morphology, histology, gene expression, receptor profile, mutation profile, aggressiveness, prognosis, and malignant characteristics. Likewise, "type" and "subtype" may be applied at a finer level, e.g., to differentiate one histological "type" into "subtypes", e.g., defined according to mutation profile or gene expression. Cancer "stage" is also used to refer to classification of cancer types based on histological and pathological characteristics relating to disease progression.

The term "neoplasm" generally refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells. The term "colorectal neoplasm-specific marker" refers to any biological material that can be used to indicate the presence of a colorectal neoplasm (e.g., a premalignant colorectal neoplasm; a malignant colorectal neoplasm).

As used herein, the term "healthy" generally refers to subject not having a colorectal cell proliferation disorder. While health is a dynamic state, as used herein, the term refers to the pathological state of a subject lacking a disease state that reference is being made to in a particular statement. In one example, when referring to a signature panel capable of classifying subjects with colorectal cancer, a healthy individual, a healthy sample, or sample from a healthy individual refers to an individual lacking colorectal cancer (CRC), advanced adenoma (AA), or benign adenoma (NAA). As used herein, the abbreviation "NAA" is used to identify samples from individuals evaluated to be negative for colorectal tumors and as such, in certain embodiments, samples identified as NAA are included in the healthy sample group. While other diseases or states of health may be present in that subject, as used herein, the term "healthy" generally indicates the lack of a stated disease for comparison or classification purposes between subjects having and lacking a disease state being discussed.

The term "minimal residual disease" or "MRD" generally refers to the small number of cancer cells in the body of a subject after cancer treatment. MRD testing may be performed to determine effectiveness of a cancer treatment and to guide further treatment plans.

As used herein, the term "screening" generally refers to examination or testing of a population of subjects at risk of suffering from a colorectal cancer or colorectal adenoma, with the objective of discriminating healthy subjects from subjects who are suffering from an undiagnosed colorectal cancer or colorectal adenoma or subjects at high risk of suffering from said indications.

As used herein, the terms "minimally-invasive biological sample" or "non-invasive sample" generally refer to any sample which is taken from the body of the patient without the need of instruments, other than fine needles used for obtaining blood from a subject. In some embodiments, minimally-invasive biological samples include blood, serum, or plasma samples.

As used herein, the terms "up-regulated" or "over-expressed" generally refer to an increase in an expression level with respect to a given "threshold value" or "cutoff value" by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more than 150%.

As used herein, the terms "threshold value" or "cutoff value," when referring to the expression levels, generally refer to a reference expression level indicative that a subject is likely to suffer from colorectal cancer or colorectal adenoma with a given sensitivity and specificity if the expression levels of the subject are above said threshold or cut-off or reference levels.

As used herein, the term "kit" is not limited to any specific device and generally includes any device suitable for working the invention such as, but not limited to, microarrays, bioarrays, biochips, biochip arrays, or bead-based assays.

Assaying Samples

The cell-free biological samples may be obtained or derived from a human subject. The cell-free biological samples may be stored in a variety of storage conditions before processing, such as different temperatures (e.g., at room temperature, under refrigeration or freezer conditions, e.g., at 25° C., at 4° C., at −18° C., −20° C., or at −80° C.) or different suspensions (e.g., EDTA collection tubes, cell-free RNA collection tubes, or cell-free DNA collection tubes).

The cell-free biological sample may be obtained from a subject with a cancer, a subject that is suspected of having a cancer, or a subject that does not have or is not suspected of having the cancer.

The cell-free biological sample may be obtained before and/or after treatment of a subject with the cancer. Cell-free biological samples may be obtained from a subject during a treatment or a treatment regime. Multiple cell-free biological samples may be obtained from a subject to monitor the effects of the treatment over time. The cell-free biological sample may be taken from a subject known or suspected of having a cancer for which a definitive positive or negative diagnosis is not available via clinical tests. The sample may be taken from a subject suspected of having cancer. The cell-free biological sample may be taken from a subject experiencing unexplained symptoms, such as fatigue, nausea, weight loss, aches and pains, weakness, or bleeding. The cell-free biological sample may be taken from a subject having explained symptoms. The cell-free biological sample may be taken from a subject at risk of developing a cancer due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

The cell-free biological sample may contain one or more analytes capable of being assayed, such as cell-free ribonucleic acid (cfRNA) molecules suitable for assaying to generate transcriptomic data, cell-free deoxyribonucleic acid (cfDNA) molecules suitable for assaying to generate genomic data, protein molecules (including autoantibodies) suitable for assaying to generate proteomic data, or a mixture or combination thereof.

After obtaining a cell-free biological sample from the subject, the cell-free biological sample may be processed to generate datasets indicative of a colon cell proliferative disorder of the subject. For example, a presence, absence, or quantitative assessment of antibody molecules of the cell-free biological sample at a panel of autoantibodies. Processing the cell-free biological sample obtained from the subject may include: (i) subjecting the cell-free biological sample to conditions that are sufficient to isolate, enrich, or extract a plurality of autoantibodies, and (ii) assaying the plurality of autoantibody molecules to generate the dataset.

The biological sample may be used directly in an assay for autoantibodies to generate an autoantibody profile for the sample. In some embodiments, the biological sample may be enriched for autoantibodies before assay (e.g., using protein-conjugated microbeads). In one embodiment, the biological sample is a plasma sample and is enriched. The biological sample may be assayed with various laboratory methodologies to determine the presence and/or concentration or level of antibodies in the biological sample. In various embodiments, such approaches may include, but are not limited to, protein microarrays, high-density protein microarrays, e.g., CDI), ELISA, Meso Scale Discovery, bead-based immunoassays (e.g. Luminex® magnetic bead-based capture assay), secondary fluoro-antibody assays, or combinations thereof to determine the autoantibody profile of a biological sample from a subject.

Signature Panels

The present disclosure provides methods and systems to analyze biological samples to obtain measurable features from a combination of autoantibody molecules identified in the sample that are associated with the development of a colon cell proliferative disorder. The collection of identified autoantibody molecules described herein possess informative value in creating classifiers for, and in models of, detection for colon cell proliferative disorders or a stage thereof. While the identified autoantibody molecules may be informative and useful individually, the autoantibody molecules may be used in combinations described herein to form a signature panel where the signature is characteristic of a colon cell proliferative disorder or a stage thereof. The features from the signature panel may be processed using a trained algorithm (e.g., a machine learning model) to create a classifier configured to stratify a population of subjects with a colon cell proliferative disorder. The methods are characterized by using one or more autoantibodies described in the signature panels. In one embodiment, a signature panel of at least 3 autoantibodies is useful for the classifiers and methods described herein.

The autoantibody signature panels described herein may allow for a quick and specific analysis of specific autoantibodies associated with colon cell proliferative disorders. The signature panels as described and employed in the methods herein may be used for the improved diagnosis, prognosis, treatment selection, and monitoring (e.g., treatment monitoring) of colon cell proliferative disorders.

The signature panels and methods provide significant improvements over current approaches to detect early-stage colon cell proliferative disorders from body fluid samples such as whole blood, plasma, or serum. Current methods used to detect and diagnose colon cell proliferative disorders include colonoscopy, sigmoidoscopy, and fecal occult blood colon cancer. In comparison to these methods, the methods provided herein may be much less invasive than colonoscopy, and equally, if not more sensitive, than sigmoidoscopy, fecal immunochemical test (FIT), and fecal occult blood test (FOBT). Methods provided herein provide significant advantages in terms of sensitivity and specificity due to the advantageous combination of using a gene panel and highly sensitive assay techniques.

The present disclosure provides methods and systems directed to autoantibody profiling of tumor antigen-associated autoantibodies ("tAAb" or "autoantibodies") associated with colon cell proliferative disorder detection and disease progression. Certain embodiments of the current invention provide autoantibodies that are differentially abundant in a sample of a subject having, or having a high risk of developing, a colon cell proliferative disorder, as compared to the corresponding sample of a subject not having, or having low risk of developing, a colon cell proliferative disorder. In one embodiment, each of the subjects having high risk of developing colon cell proliferative disorder and the subjects having low risk of developing colon cell proliferative disorder have a non-invasive precursor lesion arising within colorectal mucosa (hereinafter, colorectal lesion). The autoantibodies that are present at different abundances in a sample of a healthy subject and a subject having colon cell proliferative disorder can be used as biomarkers for diagnosis, treatment, and/or prevention of colon cell proliferative disorder.

To identify autoantibodies that are informative for the methods and classifiers described herein, the plasma from patients with colon cell proliferative disorders and plasma of subjects without colon cell proliferative disorders (control plasma or reference plasma) have been examined to identify a signature panel of autoantibodies produced by patients having a colon cell proliferative disorder in response to said colon cell proliferative disorder and their respective reactive proteins. To that end, plasma from patients with colon cell proliferative disorders and control plasma were tested using high-density protein microarrays. Protein microarrays offer a series of advantages with respect to other approaches used for identifying autoantibodies: i) the proteins printed in the array are known beforehand, thereby preventing a subsequent identification and eliminating the possible selection of mimotopes, and ii) there is no predisposition to select any protein because the proteins are all printed at a similar concentration. This combination of factors results in a high sensitivity for identifying biomarkers.

The autoantibodies identified herein can be used to identify subjects that have colon cell proliferative disorder to distinguish them from subjects that do not have colon cell proliferative disorder, or to identify subjects having a higher risk of developing colon cell proliferative disorder to distinguish them from subjects that have a lower risk of developing colon cell proliferative disorder, or to identify subjects having a colon cell proliferative disorder precursor Thus, these autoantibodies can be used as an adjunctive tool to guide decisions regarding monitoring, treatment, and management of a colon cell proliferative disorder.

In certain embodiments, disclosed herein is a panel of plasma tumor antigen-associated autoantibodies (TAAb) biomarkers useful for the early detection of colorectal proliferation disorders and relating to the early-detection of colorectal cancer.

In other embodiments, disclosed herein are detection, diagnostic, and treatment-related methods. Plasma from patients is screened for tumor antigen-associated autoantibodies (TAAb) to tumor-derived proteins as an indication of colorectal proliferation disorders.

In an aspect, the present disclosure provides an autoantibody panel characteristic of a colon cell proliferative disorder that includes immunoglobulins to 3 or more antigens selected from the group consisting of NME5, USP16, UBE2S, RNF41, CD20, ANKHD1, TXNL1, NAT6, Supt6h, PRDM8, OTUD5, PNKP, SRSF7, ASB9, NXN, ZBTB21, EYA1, GSPT1, MLIP, RBM38, ARMC5, TP53, BRD9, CDK4, PRMT6, PCOLCE, and SDCBP.

In one embodiment, the immunoglobulins are IgG, IgM, or a combination thereof.

In one embodiment, the autoantibody signature panel is useful in distinguishing healthy subjects, subjects with benign colon polyp, subjects with advanced adenoma, or subjects with colorectal cancer.

In one embodiment, the panel is useful for indicating advanced adenoma and includes IgM autoantibodies to at least 3 antigens selected from the group consisting of NME5, USP16, UBE2S, RNF41, SDCBP, and CD20. In one embodiment, the panel comprises IgM autoantibodies to UBE2, NME5, and CD20. In one embodiment, the panel is useful for indicating advanced adenoma and includes IgG autoantibodies to at least 3 antigens selected from the group consisting of ANKHD1, TXNL1, NAT6, Supt6h, PRDM8, OTUD5, PNKP, SRSF7, and ASB9. In one embodiment, the panel comprises IgG autoantibodies to ASB9, NAT6, Supt6h, and PRDM8.

In one embodiment, the panel is useful for indicating advanced adenoma and includes: 1) IgM autoantibodies to at least 3 antigens selected from the group consisting of NME5, USP16, UBE2S, RNF41, CD20, and SDCBP; 2) IgM autoantibodies to at least one antigen selected from the group consisting of UBE2S, NME5, and CD20; 3) IgG autoantibody to at least 3 antigens selected from the group consisting of ANKHD1, TXNL1, NAT6, Supt6h, PRDM8, OTUD5, PNKP, SRSF7, PCOLCE, and ASB9; 4) IgG autoantibodies to at least one antigen selected from the group consisting of ASB9, NAT6, Supt6h, and PRDM8; or combinations thereof.

In one embodiment, the panel is useful for indicating samples from subjects with benign polyps and includes IgG autoantibodies to at least 3 antigens selected from the group consisting of NXN, EYA1, GSPT1, and MLIP.

In one embodiment, the panel is useful for indicating samples from subjects with benign polyps and includes IgM autoantibodies to ZBTB21.

In one embodiment, the panel is useful for indicating colorectal cancer and includes IgM autoantibodies to at least 3 antigens selected from the group consisting of PELO, CDK4, MTCP1, PRMT6, PCOLCE, and ZBtb2. In one embodiment, the panel comprises at least 3 of IgG autoantibodies to TSSC4, BRD9, BCCIP, and TP53. In one embodiment, the panel comprises IgM autoantibodies to CDK4, PRMT6, and MTCP1. In one embodiment, the panel comprises IgG autoantibodies to TP53 and RBM38.

In one embodiment, the panel is useful for indicating colorectal cancer and includes: 1) IgM autoantibodies to at least 3 antigens selected from the group consisting of PELO, CDK4, MTP1, PRMT6, ZBTB2, and PCOLCE; 2) IgM autoantibodies to at least one antigen selected from the group consisting of CDK4, MTCP1, and PCOLCE; 3) IgG autoantibodies to at least 3 antigens selected from the group consisting of TSSC4, BRD9, BCCIP, and TP53; 4) IgG autoantibodies to TP53; or combinations thereof.

In some embodiments, a predetermined set of autoantibodies contains autoantibodies to at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, or more antigens, such as the antigens described herein. In some embodiments, a predetermined set of autoantibodies contains autoantibodies to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more antigens, such as the antigens described herein.

In some embodiments, the autoantibodies in a predetermined panel are IgM and IgG autoantibodies. In one embodiment, the autoantibodies in the predetermined panel are IgM autoantibodies. In one embodiment, the autoantibodies in the predetermined panel are IgG autoantibodies.

Classifiers, Machine Learning Models & Systems

Machine learning approaches are used to featurize the autoantibody data derived from a biological sample obtained from a subject to identify a panel of informative autoantibodies. The identified panel of informative autoantibodies for a colon cell proliferative disorder is useful to train a classifier model useful for distinguishing samples from healthy subjects and subjects having a colon cell proliferative disorder.

Further described herein is a machine learning model classifier trained on the autoantibodies described herein that are expressed in a plasma sample of a healthy subject and a plasma sample from a subject having colon cell proliferative disorder. Training a machine learning model provides a classifier having a predetermined set of autoantibody biomarkers (an "autoantibody panel" or "signature panel") useful for classifying a healthy subject or a subject having a colon cell proliferative disorder. In one example, a method is provided for a blood-based minimally-invasive autoantibody assay that can be used in a subject having a colorectal lesion to assess histologic severity. In another embodiment, the autoantibodies indicative of a colon cell proliferative disorder are detected in cell-free samples from a subject, for example, body fluid samples from a subject, such as whole blood, plasma, or serum. As such, autoantibodies disclosed herein can be used to differentiate between the presence or absence of colon cell proliferative disorder, high-risk colorectal lesions, or low-risk colorectal lesions that warrant treatment such as, surgical resection, immunotherapy, radiation, or chemotherapy, and monitoring of low-risk colorectal lesions. Monitoring and confirmation of the presence of colon cell proliferative disorder or lesions can be carried out, for example, by colonoscopy, ultrasound, MM, or CT scan.

In various examples, autoantibody features are used as input datasets into trained algorithms (e.g., machine learning models or classifiers) to find correlations between autoantibody profile and patient groups. Examples of such patient groups include presence of diseases or conditions, stages, subtypes, responders vs. non-responders, and progressors vs. non-progressors. In various examples, feature matrices are generated to compare samples obtained from subjects with known conditions or characteristics. In some embodiments, samples are obtained from healthy subjects, or subjects who do not have any of the known indications and samples from patients known to have cancer.

As used herein, as it relates to machine learning and pattern recognition, the term "feature" generally refers to an individual measurable property or characteristic of a phenomenon being observed. The concept of "feature" is related to that of an explanatory variable used in statistical techniques such as for example, but not limited to, linear regression and logistic regression. Features are usually numeric, but structural features such as strings and graphs are used in syntactic pattern recognition.

As used herein, the term "input features" (or "features") generally refers to variables that are used by the trained algorithm (e.g., model or classifier) to predict an output classification (label) of a sample, e.g., a condition, autoantibody identity, antibody sequence content (e.g., mutations), suggested data collection operations, or suggested treatments. Values of the variables may be determined for a sample and used to determine a classification.

For a plurality of assays, the system identifies feature sets to input into a trained algorithm (e.g., machine learning model or classifier). The system performs an assay on each molecule class and forms a feature vector from the measured values. The system inputs the feature vector into the machine learning model and obtains an output classification of whether the biological sample has a specified property.

In some embodiments, the machine learning model provides a classifier capable of distinguishing between two or more groups or classes of subjects or features in a population of subjects or features of the population. In some embodiments, the classifier is a trained machine learning classifier.

In some embodiments, the informative loci or features of biomarkers in a cancer tissue are assayed to form a profile. Receiver-operating characteristic (ROC) curves may be generated by plotting the performance of a particular feature (e.g., any of the biomarkers described herein and/or any item of additional biomedical information) in distinguishing between two populations (e.g., subjects responding and not responding to a therapeutic agent). In some embodiments, the feature data across the entire population (e.g., the cases and controls) are sorted in ascending order based on the value of a single feature.

In various examples, the specified property is selected from healthy vs. cancer, disease subtype, disease stage, progressor vs. non-progressor, and responder vs. non-responder.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumor, gastrointestinal carcinoid tumor, gastrointestinal stromal tumor (GIST), lymphoma, and sarcoma.

A. Data Analysis

In some examples, the present disclosure provides a system, method, or kit having data analysis realized in software application, computing hardware, or both. In various examples, the analysis application or system comprises at least a data receiving module, a data pre-processing module, a data analysis module (which can operate on one or more types of genomic data), a data interpretation module, or a data visualization module. In some embodiments, the data receiving module includes computer systems that connect laboratory hardware or instrumentation with computer systems that process laboratory data. In some embodiments, the data pre-processing module includes hardware systems or computer software that performs operations on the data in preparation for analysis. Examples of operations that may be applied to the data in the pre-processing module include affine transformations, denoising operations, data cleaning, reformatting, or subsampling. A data analysis module, which may be specialized for analyzing genomic data from one or more genomic materials, can, for example, take assembled genomic sequences and perform probabilistic and statistical analysis to identify abnormal patterns related to a disease, pathology, state, risk, condition, or phenotype. A data interpretation module can use analysis methods, for example, drawn from statistics, mathematics, or biology, to support understanding of the relation between the identified abnormal patterns and health conditions, functional states, prognoses, or risks. A data visualization module can use methods of mathematical modeling, computer graphics, or rendering to create visual representations of data that can facilitate the understanding or interpretation of results.

In various examples, machine learning methods are applied to distinguish samples in a population of samples. In some embodiments, machine learning methods are applied to distinguish samples between healthy and advanced disease (e.g., adenoma) samples.

In some embodiments, the one or more machine learning operations used to train the prediction engine include one or more of: a generalized linear model, a generalized additive model, a non-parametric regression operation, a random forest classifier, a spatial regression operation, a Bayesian regression model, a time series analysis, a Bayesian network, a Gaussian network, a decision tree learning operation, an artificial neural network, a recurrent neural network, a reinforcement learning operation, linear or non-linear regression operations, a support vector machine, a clustering operation, and a genetic algorithm operation.

In various examples, computer processing methods are selected from the group consisting of logistic regression, multiple linear regression (MLR), dimension reduction, partial least squares (PLS) regression, principal component regression, autoencoders, variational autoencoders, singular value decomposition, Fourier bases, wavelets, discriminant analysis, support vector machine, decision tree, classification and regression trees (CART), tree-based methods, random forest, gradient boost tree, logistic regression, matrix factorization, multidimensional scaling (MDS), dimensionality reduction methods, t-distributed stochastic neighbor embedding (t-SNE), multilayer perceptron (MLP), network clustering, neuro-fuzzy, and artificial neural networks.

In some examples, the methods disclosed herein can include computational analysis on nucleic acid sequencing data of samples from a subject or from a plurality of subjects.

B. Classifier Generation

In an aspect, systems and methods disclosed herein provide a classifier generated based on feature information derived from autoantibody analysis from biological samples containing autoantibodies. The classifier forms part of a predictive engine for distinguishing groups in a population based on features identified in biological samples such as autoantibodies. A collective representation of the autoantibody information in a biological sample can be referred to as an autoantibody profile.

In some embodiments, a classifier is created by normalizing the autoantibody information by formatting similar portions of the autoantibody information into a unified format and a unified scale; storing the normalized autoantibody information in a columnar database; training a prediction engine by applying one or more one machine learning operations to the stored normalized autoantibody information, the prediction engine mapping, for a particular population, a combination of one or more features; applying the prediction engine to the accessed field information to identify a subject associated with a group; and classifying the subject into a group.

Specificity, as used herein, generally refers to "the probability of a negative test among those who are free from the disease." Specificity may be calculated by the number of disease-free persons who tested negative divided by the total number of disease-free subjects.

In various examples, the model, classifier, or predictive test has a specificity of at least 40%, at least 45%, at least 50%, at least 55%, at least 60%, at least 65%, at least 70%, at least 75%, at least 80%, at least 85%, at least 90%, at least 95%, or at least 99%.

Sensitivity, as used herein, generally refers to "the probability of a positive test among those who have the disease." Sensitivity may be calculated by the number of diseased subjects who tested positive divided by the total number of diseased subjects.

In various examples, the model, classifier, or predictive test has a sensitivity of at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

C. Digital Processing Device

In some embodiments, described herein is a digital processing device or use of the same. In some examples, the digital processing device can include one or more hardware central processing units (CPU), graphics processing units (GPU), or tensor processing units (TPU) that carry out the device's functions. In some examples, the digital processing device can include an operating system configured to perform executable instructions.

In some examples, the digital processing device can optionally be connected to a computer network. In some examples, the digital processing device may be optionally connected to the Internet. In some examples, the digital processing device may be optionally connected to a cloud computing infrastructure. In some examples, the digital processing device may be optionally connected to an intranet. In some examples, the digital processing device may be optionally connected to a data storage device.

Non-limiting examples of suitable digital processing devices include server computers, desktop computers, laptop computers, notebook computers, sub-notebook computers, netbook computers, netpad computers, set-top computers, handheld computers, Internet appliances, mobile smartphones, and tablet computers. Suitable tablet computers can include, for example, those with booklet, slate, and convertible configurations.

In some examples, the digital processing device can include an operating system configured to perform executable instructions. For example, the operating system can include software, including programs and data, which manages the device's hardware and provides services for execution of applications. Non-limiting examples of operating systems include Ubuntu, FreeBSD, OpenBSD, NetBSD®, Linux, Apple® Mac OS X Server®, Oracle® Solaris®, Windows Server®, and Novell® NetWare®. Non-limiting examples of suitable personal computer operating systems include Microsoft® Windows®, Apple® Mac OS X®, UNIX®, and UNIX-like operating systems such as GNU/Linux®. In some examples, the operating system may be provided by cloud computing, and cloud computing resources may be provided by one or more service providers.

In some examples, the device can include a storage and/or memory device. The storage and/or memory device may be one or more physical apparatuses used to store data or programs on a temporary or permanent basis. In some examples, the device may be volatile memory and require power to maintain stored information. In some examples, the device may be non-volatile memory and retain stored information when the digital processing device is not powered. In some examples, the non-volatile memory can include flash memory. In some examples, the non-volatile memory can include dynamic random-access memory (DRAM). In some examples, the non-volatile memory can include ferroelectric random access memory (FRAM). In some examples, the non-volatile memory can include phase-change random access memory (PRAM).

In some examples, the device may be a storage device including, for example, CD-ROMs, DVDs, flash memory devices, magnetic disk drives, magnetic tapes drives, optical disk drives, and cloud computing-based storage. In some examples, the storage and/or memory device may be a combination of devices such as those disclosed herein. In some examples, the digital processing device can include a display to send visual information to a user. In some examples, the display may be a cathode ray tube (CRT). In some examples, the display may be a liquid crystal display (LCD). In some examples, the display may be a thin film transistor liquid crystal display (TFT-LCD). In some examples, the display may be an organic light emitting diode (OLED) display. In some examples, an OLED display may be a passive-matrix OLED (PMOLED) or active-matrix OLED (AMOLED) display. In some examples, the display may be a plasma display. In some examples, the display may be a video projector. In some examples, the display may be a combination of devices such as those disclosed herein.

In some examples, the digital processing device can include an input device to receive information from a user. In some examples, the input device may be a keyboard. In some examples, the input device may be a pointing device including, for example, a mouse, trackball, track pad, joystick, game controller, or stylus. In some examples, the input device may be a touch screen or a multi-touch screen. In some examples, the input device may be a microphone to capture voice or other sound input. In some examples, the input device may be a video camera to capture motion or visual input. In some examples, the input device may be a combination of devices such as those disclosed herein.

D. Non-Transitory Computer-Readable Storage Medium

In some examples, the subject matter disclosed herein can include one or more non-transitory computer-readable storage media encoded with a program including instructions executable by the operating system of an optionally networked digital processing device. In some examples, a computer-readable storage medium may be a tangible component of a digital processing device. In some examples, a computer-readable storage medium may be optionally removable from a digital processing device. In some examples, a computer-readable storage medium can include, for example, CD-ROMs, DVDs, flash memory devices, solid state memory, magnetic disk drives, magnetic tape drives, optical disk drives, cloud computing systems and services, and the like. In some examples, the program and instructions may be permanently, substantially permanently, semi-permanently, or non-transitorily encoded on the media.

E. Computer Systems

The present disclosure provides computer systems that are programmed to implement methods described herein. FIG. 1 shows a computer system 101 that is programmed or otherwise configured to store, process, identify, or interpret patient data, biological data, biological sequences, reference sequences, and autoantibody profiles. The computer system 101 can process various aspects of patient data, biological data, biological sequences, reference sequences, and autoantibody profiles of the present disclosure. The computer system 101 may be an electronic device of a user or a computer system that is remotely located with respect to the electronic device. The electronic device may be a mobile electronic device.

The computer system 101 comprises a central processing unit (CPU, also "processor" and "computer processor" herein) 105, which may be a single core or multi core processor, or a plurality of processors for parallel processing. The computer system 101 also comprises memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120, and peripheral devices 125 are in communication with the CPU 105 through a communication bus (solid lines), such as a motherboard. The storage unit 115 may be a data storage unit (or data repository) for storing data. The computer system 101 may be operatively coupled to a computer network ("network") 130 with the aid of the communication interface 120. The network 130 may be the Internet, an internet and/or extranet, or an intranet and/or extranet that is in communication with the Internet. The network 130 in some examples is a telecommunication and/or data network. The network 130 can include one or more computer servers, which can enable distributed computing, such as cloud computing. The network 130, in some examples, with the aid of the computer system 101, can implement a peer-to-peer network, which may enable devices coupled to the computer system 101 to behave as a client or a server.

The CPU 105 can execute a sequence of machine-readable instructions, which may be embodied in a program or software. The instructions may be stored in a memory location, such as the memory 110. The instructions may be directed to the CPU 105, which can subsequently program or otherwise configure the CPU 105 to implement methods of the present disclosure. Examples of operations performed by the CPU 105 can include fetch, decode, execute, and writeback.

The CPU 105 may be part of a circuit, such as an integrated circuit. One or more other components of the system 101 may be included in the circuit. In some examples, the circuit is an application specific integrated circuit (ASIC).

The storage unit 115 can store files, such as drivers, libraries, and saved programs. The storage unit 115 can store user data, e.g., user preferences and user programs. The computer system 101 in some examples can include one or more additional data storage units that are external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants. The user can access the computer system 101 via the network 130.

Methods as described herein may be implemented by way of machine (e.g., computer processor) executable code stored on an electronic storage location of the computer system 101, such as, for example, on the memory 110 or electronic storage unit 115. The machine-executable or machine-readable code may be provided in the form of software. During use, the code may be executed by the processor 105. In some examples, the code may be retrieved from the storage unit 115 and stored on the memory 110 for ready access by the processor 105. In some examples, the electronic storage unit 115 may be precluded, and machine-executable instructions are stored on memory 110.

The code may be pre-compiled and configured for use with a machine having a processer adapted to execute the code or may be interpreted or compiled during runtime. The code may be supplied in a programming language that may be selected to enable the code to execute in a pre-compiled, interpreted, or as-compiled fashion.

Aspects of the systems and methods provided herein, such as the computer system 101, may be embodied in programming. Various aspects of the technology may be thought of as "products" or "articles of manufacture" typically in the form of machine (or processor) executable code and/or associated data that is carried on or embodied in a type of machine readable medium. Machine-executable code may be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements comprises optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" generally refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 can include or be in communication with an electronic display 135 that comprises a user interface (UI) 140 for providing, for example, a nucleic acid sequence, an enriched nucleic acid sample, an autoantibody profile, an expression profile, and an analysis of a RNA expression profile. Examples of UIs include, without limitation, a graphical user interface (GUI) and web-based user interface.

Methods and systems of the present disclosure may be implemented by way of one or more algorithms. An algorithm may be implemented by way of software upon execution by the central processing unit 105. The algorithm can, for example, store, process, identify, or interpret patient data, biological data, biological sequences, and reference sequences.

While certain examples of methods and systems have been shown and described herein, one of skill in the art will realize that these are provided by way of example only and not intended to be limiting within the specification. Numerous variations, changes, and substitutions will now occur to those skilled in the art without departing from the scope described herein. Furthermore, it shall be understood that all aspects of the described methods and systems are not limited to the specific depictions, configurations or relative proportions set forth herein which depend upon a variety of conditions and variables and the description is intended to include such alternatives, modifications, variations, or equivalents.

In some examples, the subject matter disclosed herein can include at least one computer program or use of the same. A computer program can be a sequence of instructions, executable in the digital processing device's CPU, GPU, or TPU, written to perform a specified task. Computer-readable instructions may be implemented as program modules, such as functions, objects, Application Programming Interfaces (APIs), data structures, and the like, that perform particular tasks or implement particular abstract data types. In light of the disclosure provided herein, a computer program may be written in various versions of various languages.

The functionality of the computer-readable instructions may be combined or distributed as desired in various environments. In some examples, a computer program can include one sequence of instructions. In some examples, a computer program can include a plurality of sequences of instructions. In some examples, a computer program may be provided from one location. In some examples, a computer program may be provided from a plurality of locations. In some examples, a computer program can include one or more software modules. In some examples, a computer program can include, in part or in whole, one or more web applications, one or more mobile applications, one or more standalone applications, one or more web browser plug-ins, extensions, add-ins, or add-ons, or combinations thereof.

In some examples, the computer processing may be a method of statistics, mathematics, biology, or any combination thereof. In some examples, the computer processing method comprises a dimension reduction method including, for example, logistic regression, dimension reduction, principal component analysis, autoencoders, singular value decomposition, Fourier bases, singular value decomposition, wavelets, discriminant analysis, support vector machine, tree-based methods, random forest, gradient boost tree, logistic regression, matrix factorization, network clustering, and neural network.

In some examples, the computer processing method is a supervised machine learning method including, for example, a regression, support vector machine, tree-based method, and network.

In some examples, the computer processing method is an unsupervised machine learning method including, for example, clustering, network, principal component analysis, and matrix factorization.

F. Databases

In some examples, the subject matter disclosed herein can include one or more databases, or use of the same to store patient data, biological data, biological sequences, reference sequences, or autoantibody profiles. Reference sequences may be derived from a database. In view of the disclosure provided herein, many databases may be suitable for storage and retrieval of the sequence information. In some examples, suitable databases can include, for example, relational databases, non-relational databases, object-oriented databases, object databases, entity-relationship model databases, associative databases, and XML databases. In some examples, a database may be internet-based. In some examples, a database may be web-based. In some examples, a database may be cloud computing-based. In some examples, a database may be based on one or more local computer storage devices.

In an aspect, the present disclosure provides a non-transitory computer-readable medium comprising instructions that direct a processor to carry out a method disclosed herein.

In an aspect, the present disclosure provides a computing device comprising the computer-readable medium.

In another aspect, the present disclosure provides a system for performing classifications of biological samples, comprising:
  a) a receiver to receive a plurality of training samples, each of the plurality of training samples having a plurality of classes of molecules, wherein each of the plurality of training samples comprises one or more known labels;
  b) a feature module to identify a set of features corresponding to an assay that are operable to be input to the machine learning model for each of the plurality of training samples, wherein the set of features correspond to properties of molecules in the plurality of training samples, wherein for each of the plurality of training samples, the system is operable to subject a plurality of classes of molecules in the training sample to a plurality of different assays to obtain sets of measured values, wherein each set of measured values is from one assay applied to a class of molecules in the training sample, wherein a plurality of sets of measured values are obtained for the plurality of training samples;

c) an analysis module to analyze the sets of measured values to obtain a training vector for the training sample, wherein the training vector comprises feature values of the N set of features of the corresponding assay, each feature value corresponding to a feature and including one or more measured values, wherein the training vector is formed using at least one feature from at least two of the N sets of features corresponding to a first subset of the plurality of different assays;

d) a labeling module to inform the system on the training vectors using parameters of the machine learning model to obtain output labels for the plurality of training samples;

e) a comparator module to compare the output labels to the known labels of the training samples;

f) a training module to iteratively search for optimal values of the parameters as part of training the machine learning model based on the comparing of the output labels to the known labels of the training samples; and g) an output module to provide the parameters of the machine learning model and the set of features for the machine learning model.

Methods of Classifying Subjects in a Population

The disclosed methods are directed to ascertaining parameters of autoantibody expression associated with colon cell proliferative disorders via analysis of expressed autoantibodies in a subject. The method is for use in the improved diagnosis, treatment and monitoring of colon cell proliferative disorders, more specifically by enabling the improved identification of and differentiation between stages or subclasses of said disorder and the genetic predisposition to said disorders.

In some embodiments, the method comprises analyzing differential expression of autoantibodies in a biological sample from a subject in a population.

Generally, the present disclosure provides a method for detecting a colon cell proliferative disorder that may be applied to cell-free samples, e.g., to detect the presence and characteristics of autoantibodies between subjects with and without a colon cell proliferative disorder or between different colon cell proliferative disorders. The method utilizes detection of autoantibodies as the basic "positive" or "negative" for a colon cell proliferative disorder signal compared to a healthy subject not having a colon cell proliferative disorder.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumor, gastrointestinal carcinoid tumor, gastrointestinal stromal tumor (GIST), lymphoma, and sarcoma.

In a third aspect, the present disclosure provides a method for determining an autoantibody profile of a biological sample from a subject, comprising:

a) obtaining the biological sample containing autoantibodies from the subject; and b) measuring an amount of an autoantibody from a predetermined panel of autoantibodies comprising autoantibodies to 3 or more antigens selected from the group consisting of NME5, USP16, UBE2S, RNF41, CD20, ANKHD1, TXNL1, NAT6, Supt6h, PRDM8, OTUD5, PNKP, SRSF7, ASB9, NXN, ZBTB21, EYA1, GSPT1, MLIP, RBM38, ARMC5, TP53, BRD9, CDK4, PRMT6, PCOLCE, and SDCBP, to provide the autoantibody profile of the subject.

In some embodiments, the autoantibody profile is associated with a colon cell proliferative disorder and provides classification of the subject as having a colon cell proliferative disorder.

In some embodiments, the biological sample obtained from the subject is selected from the group consisting of body fluids, stool, colonic effluent, urine, blood plasma, blood serum, whole blood, isolated blood cells, cells isolated from the blood, and combinations thereof.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumor, gastrointestinal carcinoid tumor, gastrointestinal stromal tumor (GIST), lymphoma, and sarcoma.

In some embodiments, the colon cell proliferative disorder is selected from the group consisting of stage 1 colorectal cancer, stage 2 colorectal cancer, stage 3 colorectal cancer, and stage 4 colorectal cancer.

In some embodiments, the advanced adenoma is a tubular adenoma, a tubulovillous adenoma, a villous adenoma, an adenocarcinoma, or a hyperplastic polyp.

In a fourth aspect, the present disclosure provides a method for detecting a colon cell proliferative disorder in a subject, comprising:

a) obtaining a biological sample containing autoantibodies from the subject;

b) measuring an amount of an autoantibody from a predetermined panel of autoantibodies comprising autoantibodies to 3 or more antigens selected from the group consisting of NME5, USP16, UBE2S, RNF41, CD20, ANKHD1, TXNL1, NAT6, Supt6h, PRDM8, OTUD5, PNKP, SRSF7, ASB9, NXN, ZBTB21, EYA1, GSPT1, MLIP, RBM38, ARMC5, TP53, BRD9, CDK4, PRMT6, PCOLCE, and SDCBP, to provide an autoantibody profile of the subject; and c) processing the autoantibody profile using a machine learning model trained to be capable of distinguishing between healthy subjects and subjects with the colon cell proliferative disorder to provide an output value associated with presence of the colon cell proliferative disorder, thereby indicating the presence of the colon cell proliferative disorder in the subject.

In some embodiments, the biological sample obtained from the subject is selected from the group consisting of body fluids, stool, colonic effluent, urine, blood plasma, blood serum, whole blood, isolated blood cells, cells isolated from the blood, and combinations thereof.

In another aspect, the invention relates to a method for detecting binding of an autoantibody to a protein to generate an autoantibody profile of a sample which comprises:

a) contacting a biological sample with the protein or a fragment thereof susceptible of being recognized by the autoantibody; and b) detecting formation of an autoantibody-protein complex formed by binding of the autoantibody to the protein or fragment thereof, wherein the protein is selected from the group consisting of NME5, USP16, UBE2S, RNF41, CD20, ANKHD1, TXNL1, NAT6, Supt6h, PRDM8, OTUD5, PNKP, SRSF7, ASB9, NXN, ZBTB21, EYA1, GSPT1, MLIP, RBM38, ARMC5, TP53, BRD9, CDK4, PRMT6, PCOLCE, and SDCBP, to provide the autoantibody profile of the sample.

In another aspect, the invention relates to a method of obtaining data in a biological sample from a subject which comprises detecting at least 3 autoantibodies to a protein, wherein the at least 3 autoantibodies are selected from the group consisting of an autoantibody to the UBE2S protein, an autoantibody to the CD20 protein, an autoantibody to the ASB9 protein, an autoantibody to the PRDM8 protein, an autoantibody to the CDK4 protein, an autoantibody to the MTCP1 protein, and an autoantibody to the TP53 protein. In some embodiments, the method further comprises determining a level of the autoantibody in the sample.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumor, gastrointestinal carcinoid tumor, gastrointestinal stromal tumor (GISTs), lymphoma, and sarcoma.

In some embodiments, the colon cell proliferative disorder is selected from the group consisting of stage 1 colorectal cancer, stage 2 colorectal cancer, stage 3 colorectal cancer, and stage 4 colorectal cancer.

In another aspect, the present disclosure provides a method for determining an autoantibody profile of a biological sample from a subject, comprising:
a) obtaining the biological sample containing autoantibodies from the subject;
b) measuring an amount of an autoantibody from a predetermined panel of autoantibodies comprising autoantibodies to 3 or more antigens selected from the group consisting of NME5, USP16, UBE2S, RNF41, CD20, ANKHD1, TXNL1, NAT6, Supt6h, PRDM8, OTUD5, PNKP, SRSF7, ASB9, NXN, ZBTB21, EYA1, GSPT1, MLIP, RBM38, ARMC5, TP53, BRD9, CDK4, PRMT6, PCOLCE, and SDCBP, to provide the autoantibody profile of the subject.

In another aspect, the present disclosure provides a method for detecting a colon cell proliferative disorder in a subject, comprising:
a) obtaining a biological sample containing autoantibodies from a subject;
b) measuring an amount of an autoantibody from a predetermined panel of autoantibodies comprising autoantibodies to 3 or more antigens selected from the group consisting of NME5, USP16, UBE2S, RNF41, CD20, ANKHD1, TXNL1, NAT6, Supt6h, PRDM8, OTUD5, PNKP, SRSF7, ASB9, NXN, ZBTB21, EYA1, GSPT1, MLIP, RBM38, ARMC5, TP53, BRD9, CDK4, PRMT6, PCOLCE, and SDCBP, to provide an autoantibody profile of the subject;
c) processing the autoantibody profile of the subject using a machine learning model trained to distinguish between subjects not having the colon cell proliferative disorder and subjects having the colon cell proliferative disorder; and
d) determining, using the machine learning model based at least in part on the autoantibody profile, a value associated with subjects having the colon cell proliferative disorder, thereby detecting the colon cell proliferative disorder in the subject.

In another aspect, the present disclosure provides a method for monitoring minimal residual disease in a subject previously treated for disease, comprising: determining an autoantibody profile of a biological sample from the subject using a panel of autoantibodies comprising autoantibodies to antigens selected from the group consisting of NME5, USP16, UBE2S, RNF41, CD20, ANKHD1, TXNL1, NAT6, Supt6h, PRDM8, OTUD5, PNKP, SRSF7, ASB9, NXN, ZBTB21, EYA1, GSPT1, MLIP, RBM38, ARMC5, TP53, BRD9, CDK4, PRMT6, PCOLCE, and SDCBP, thereby generating a baseline autoantibody state; and determining an autoantibody profile of a biological sample obtained from the subject at one or more time points after the generating of the baseline autoantibody state, thereby generating a current autoantibody state, wherein a change between the baseline autoantibody state and the current autoantibody state indicates a change in the minimal residual disease in the subject.

The trained machine learning methods, models, and discriminate classifiers described herein may be applied toward various medical applications including cancer detection, diagnosis and treatment responsiveness. As models may be trained with subject metadata and analyte-derived features, the applications may be tailored to stratify subjects in a population and guide treatment decisions accordingly.

Diagnosis

Methods and systems provided herein may perform predictive analytics using artificial intelligence-based approaches to analyze acquired data from a subject (patient) to generate an output of diagnosis of the subject having cancer (e.g., colorectal cancer). For example, the application may apply a prediction algorithm to the acquired data to generate the diagnosis of the subject having the cancer. The prediction algorithm may comprise an artificial intelligence-based predictor, such as a machine learning-based predictor, configured to process the acquired data to generate the diagnosis of the subject having the cancer.

The machine learning predictor may be trained using datasets, e.g., datasets generated by performing autoantibody assays using the signature panels described herein on biological samples of subjects from one or more sets of cohorts of patients having cancer as inputs and known diagnosis (e.g., staging and/or tumor fraction) outcomes of the subjects as outputs to the machine learning predictor.

Training datasets (e.g., datasets generated by performing autoantibody assays using the signature panels described herein on biological samples of subjects) may be generated from, for example, one or more sets of subjects having common characteristics (features) and outcomes (labels). Training datasets may comprise a set of features and labels corresponding to the features relating to diagnosis. Features may comprise characteristics such as, for example, certain ranges or categories of autoantibody assay measurements, such as the presence or characteristics of an autoantibody in a biological sample obtained from a healthy and disease. For example, a set of features collected from a given subject at a given time point may collectively serve as a diagnostic signature, which may be indicative of an identified cancer of the subject at the given time point. Characteristics may also include labels indicating the subject's diagnostic outcome, such as for one or more cancers.

Labels may comprise outcomes such as, for example, a known diagnosis (e.g., staging and/or tumor fraction) outcomes of the subject. Outcomes may include a characteristic associated with the cancers in the subject. For example, characteristics may be indicative of the subject having one or more cancers.

Training sets (e.g., training datasets) may be selected by random sampling of a set of data corresponding to one or more sets of subjects (e.g., retrospective and/or prospective cohorts of patients having or not having one or more cancers). Alternatively, training sets (e.g., training datasets) may be selected by proportionate sampling of a set of data corresponding to one or more sets of subjects (e.g., retrospective and/or prospective cohorts of patients having or not having one or more cancers). Training sets may be balanced across sets of data corresponding to one or more sets of subjects (e.g., patients from different clinical sites or trials). The machine learning predictor may be trained until certain predetermined conditions for accuracy or performance are satisfied, such as having minimum desired values corresponding to diagnostic accuracy measures. For example, the diagnostic accuracy measure may correspond to prediction of a diagnosis, staging, or tumor fraction of one or more cancers in the subject.

Examples of diagnostic accuracy measures may include sensitivity, specificity, positive predictive value (PPV), negative predictive value (NPV), accuracy, and area under the curve (AUC) of a Receiver Operating Characteristic (ROC) curve corresponding to the diagnostic accuracy of detecting or predicting the cancer (e.g., colorectal cancer).

In an aspect, the disclosure provides a method of using a classifier capable of distinguishing a population of subjects, comprising:
 a) obtaining a biological sample containing autoantibodies from a subject;
 b) measuring an amount of an autoantibody from a predetermined panel of autoantibodies comprising autoantibodies to 3 or more antigens selected from the group consisting of NME5, USP16, UBE2S, RNF41, CD20, ANKHD1, TXNL1, NAT6, Supt6h, OTUD5, PNKP, SRSF7, ASB9, PRDM8, NXN, ZBTB21, EYA1, GSPT1, MLIP, RBM38, ARMC5, TP53, BRD9, CDK4, PRMT6, PCOLCE, and SDCBP, to provide an autoantibody profile of the subject;
 c) processing the autoantibody profile of the subject using a machine learning model trained to distinguish in two or more populations; and
 d) determining using by the machine learning model based at least in part on the autoantibody profile a value associated with the populations, thereby distinguishing a population of subjects.

In another aspect, the present disclosure provides a method for identifying a cancer in a subject, comprising:
 a) obtaining a biological sample containing autoantibodies from a subject;
 b) measuring an amount of an autoantibody from a predetermined panel of autoantibodies comprising autoantibodies to 3 or more antigens selected from the group consisting of NME5, USP16, UBE2S, RNF41, CD20, ANKHD1, TXNL1, NAT6, Supt6h, PRDM8, OTUD5, PNKP, SRSF7, ASB9, NXN, ZBTB21, EYA1, GSPT1, MLIP, RBM38, ARMC5, TP53, BRD9, CDK4, PRMT6, PCOLCE, and SDCBP, to provide an autoantibody profile of the subject; and
 c) processing the autoantibody profile using a machine learning model trained to be capable of distinguishing between healthy subjects and subjects with a colon cell proliferative disorder to provide an output value associated with presence of a colon cell proliferative disorder, thereby indicating the presence of a colon cell proliferative disorder in the subject to generate a likelihood of said subject having said cancer.

A variety of statistical and mathematical methods for establishing the threshold or cutoff level of expression may be used. A threshold or cutoff expression level for a particular biomarker may be selected, for example, based on data from Receiver Operating Characteristic (ROC) plots, as described in the Examples and Figures disclosed herein. One of skill in the art will appreciate that these threshold or cutoff expression levels can be varied, for example, by moving along the ROC plot for a particular biomarker or combinations thereof, to obtain different values for sensitivity or specificity thereby affecting overall assay performance. For example, if the objective is to have a robust diagnostic method from a clinical point of view, high sensitivity should be prioritized. However, if the goal is to have a cost-effective method, high specificity should be prioritized. The best cutoff refers to the value obtained from the ROC plot for a particular biomarker that produces the best sensitivity and specificity. Sensitivity and specificity values are calculated over the range of thresholds (cutoffs). Thus, the threshold or cutoff values can be selected such that the sensitivity and/or specificity are at least about 50%, and can be, for example, at least 55%, at least 60%, at least 65%, at least 70%, at least 75%, at least 80%, at least 85%, at least 90%, at least 95%, at least 96%, at least 97%, at least 98%, at least 99% or at least 100% in at least 60% of the patient population assayed, or in at least 65%, at least 70%, at least 75%, or at least 80% of the patient population assayed.

Consequently, some embodiments of the present invention are carried out by determining the presence and/or levels of at least the autoantibodies previously cited in a minimally-invasive sample isolated from the subject to be diagnosed or screened, and comparing the presence and/or levels of the autoantibodies with predetermined threshold or cutoff values, wherein the predetermined threshold or cutoff values correspond to the expression level of said autoantibodies which correlates with the highest specificity at a desired sensitivity in a ROC curve calculated based at least in part on the expression levels of the autoantibodies determined in a patient population being at risk of suffering colorectal cancer or colorectal adenoma, wherein the overexpression of at least one of said autoantibodies with respect to said predetermined cutoff value is indicative that the subject suffers from colorectal cancer or colorectal adenoma with said desired sensitivity.

As another example, such a predetermined condition may be that the specificity of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the positive predictive value (PPV) of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the negative predictive value (NPV) of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the area under the curve (AUC) of a Receiver Operating Characteristic (ROC) curve of predicting the colon cell proliferative disorder comprises a value of at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

Monitoring Colorectal Cancer

After using a trained algorithm to process the dataset, the colorectal cancer may be identified or monitored in the subject. The identification may be based at least in part on quantitative measures of sequence reads of the dataset at a panel of colorectal cancer-associated autoantibodies.

In some embodiments, methods disclosed herein may be applied to monitor and/or predict tumor load.

In some embodiments, methods disclosed herein may be applied to detect and/or predict residual tumor post-surgery.

In some embodiments, methods disclosed herein may be applied to detect and/or predict minimal residual disease post-treatment.

In some embodiments, methods disclosed herein may be applied to detect and/or predict relapse.

In an aspect, methods disclosed herein may be applied as a secondary screen.

In an aspect, methods disclosed herein may be applied as a primary screen.

In an aspect, methods disclosed herein may be applied to monitor cancer development.

In an aspect, methods disclosed herein may be applied to monitor and/or predict cancer risk.

The colorectal cancer may be identified in the subject at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The accuracy of identifying the colorectal cancer by the trained algorithm may be calculated as the percentage of independent test samples (e.g., subjects known to have the colorectal cancer or subjects with negative clinical test results for the colorectal cancer) that are correctly identified or classified as having or not having the colorectal cancer.

The colorectal cancer may be identified in the subject with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the colorectal cancer using the trained algorithm may be calculated as the percentage of cell-free biological samples identified or classified as having the colorectal cancer that correspond to subjects that truly have the colorectal cancer.

The colorectal cancer may be identified in the subject with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the colorectal cancer using the trained algorithm may be calculated as the percentage of cell-free biological samples identified or classified as not having the colorectal cancer that correspond to subjects that truly do not have the colorectal cancer.

The colorectal cancer may be identified in the subject with a clinical sensitivity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the colorectal cancer using the trained algorithm may be calculated as the percentage of independent test samples associated with presence of the colorectal cancer (e.g., subjects known to have the colorectal cancer) that are correctly identified or classified as having the colorectal cancer.

The colorectal cancer may be identified in the subject with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the colorectal cancer using the trained algorithm may be calculated as the percentage of independent test samples associated with absence of the colorectal cancer (e.g., subjects with negative clinical test results for the colorectal cancer) that are correctly identified or classified as not having the colorectal cancer.

In some embodiments, the trained algorithm may determine that the subject is at risk of colorectal cancer of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

The trained algorithm may determine that the subject is at risk of colorectal cancer at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more.

Upon identifying the subject as having the colorectal cancer, the subject may be optionally provided with a therapeutic intervention (e.g., prescribing an appropriate course of treatment to treat the colorectal cancer of the subject). The therapeutic intervention may comprise a prescription of an effective dose of a drug, a further testing or evaluation of the colorectal cancer, a further monitoring of the colorectal cancer, or a combination thereof. If the subject is currently being treated for the colorectal cancer with a course of treatment, the therapeutic intervention may comprise a subsequent different course of treatment (e.g., to increase treatment efficacy due to non-efficacy of the current course of treatment).

The therapeutic intervention may comprise recommending the subject for a secondary clinical test to confirm a diagnosis of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

The colorectal cancer of the subject may be monitored by monitoring a course of treatment for treating the colorectal cancer of the subject. The monitoring may comprise assessing the colorectal cancer of the subject at two or more time points. The assessing may be based at least on the quantitative measures of autoantibodies of the dataset at a panel of colorectal cancer-associated autoantibodies comprising quantitative measures of a panel of colorectal cancer-associated autoantibodies determined at each of the two or more time points.

In some embodiments, a difference in the quantitative measures of sequence reads of the dataset at a panel of colorectal cancer-associated autoantibodies comprising quantitative measures of a panel of colorectal cancer-associated autoantibodies determined between the two or more time points may be indicative of one or more clinical indications, such as (i) a diagnosis of the colorectal cancer of the subject, (ii) a prognosis of the colorectal cancer of the subject, (iii) an increased risk of the colorectal cancer of the subject, (iv) a decreased risk of the colorectal cancer of the subject, (v) an efficacy of the course of treatment for treating the colorectal cancer of the subject, and (vi) a non-efficacy of the course of treatment for treating the colorectal cancer of the subject.

In some embodiments, a difference in the quantitative measures of autoantibodies comprising quantitative measures of a panel of colorectal cancer-associated autoantibodies determined between the two or more time points may be indicative of a diagnosis of the colorectal cancer of the subject. For example, if the colorectal cancer was not detected in the subject at an earlier time point but was detected in the subject at a later time point, then the difference is indicative of a diagnosis of the colorectal cancer of the subject. A clinical action or decision may be made based at least in part on this indication of diagnosis of the colorectal cancer of the subject, such as, for example, prescribing a new therapeutic intervention for the subject. The clinical action or decision may comprise recommending the subject for a secondary clinical test to confirm the diagnosis of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of autoantibodies of the dataset at a panel of colorectal cancer-associated autoantibodies comprising quantitative measures of a panel of colorectal cancer-associated autoantibodies determined between the two or more time points may be indicative of a prognosis of the colorectal cancer of the subject.

In some embodiments, a difference in the quantitative measures of autoantibodies of the dataset at a panel of colorectal cancer-associated autoantibodies comprising quantitative measures of a panel of colorectal cancer-associated autoantibodies determined between the two or more time points may be indicative of the subject having an increased risk of the colorectal cancer. For example, if the colorectal cancer was detected in the subject both at an earlier time point and at a later time point, and if the difference is a positive difference (e.g., the quantitative measures of autoantibodies of the dataset at a panel of colorectal cancer-associated autoantibodies increased from the earlier time point to the later time point), then the difference may be indicative of the subject having an increased risk of the colorectal cancer. A clinical action or decision may be made based at least in part on this indication of the increased risk of the colorectal cancer, e.g., prescribing a new therapeutic intervention or switching therapeutic interventions (e.g., ending a current treatment and prescribing a new treatment) for the subject. The clinical action or decision may comprise recommending the subject for a secondary clinical test to confirm the increased risk of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of sequence reads of the dataset at a panel of colorectal cancer-associated autoantibodies comprising quantitative measures of a panel of colorectal cancer-associated autoantibodies determined between the two or more time points may be indicative of the subject having a decreased risk of the colorectal cancer. For example, if the colorectal cancer was detected in the subject both at an earlier time point and at a later time point, and if the difference is a negative difference (e.g., the quantitative measures of autoantibodies of the dataset at a panel of colorectal cancer-associated autoantibodies comprising quantitative measures of a panel of colorectal cancer-associated autoantibodies decreased from the earlier time point to the later time point), then the difference may be indicative of the subject having a decreased risk of the colorectal cancer. A clinical action or decision may be made based at least in part on this indication of the decreased risk of the colorectal cancer (e.g., continuing or ending a current therapeutic intervention) for the subject. The clinical action or decision may comprise recommending the subject for a secondary clinical test to confirm the decreased risk of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of sequence reads of the dataset at a panel of colorectal cancer-associated autoantibodies comprising quantitative measures of a panel of colorectal cancer-associated autoantibodies determined between the two or more time points may be indicative of an efficacy of the course of treatment for treating the colorectal cancer of the subject. For example, if the colorectal cancer was detected in the subject at an earlier time point but was not detected in the subject at a later time point, then the difference may be indicative of an efficacy of the course of treatment for treating the colorectal cancer of the subject. A clinical action or decision may be made based at least in part on this indication of the efficacy of the course of treatment for treating the colorectal cancer of the subject, e.g., continuing or ending a current therapeutic intervention for the subject. The clinical action or decision may comprise recommending the subject for a secondary clinical test to confirm the efficacy of the course of treatment for treating the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of autoantibodies of the dataset at a panel of colorectal cancer-associated autoantibodies comprising quantitative measures of a panel of colorectal cancer-associated autoantibodies determined between the two or more time points may be indicative of a non-efficacy of the course of treatment for treating the colorectal cancer of the subject. For example, if the colorectal cancer was detected in the subject both at an earlier time point and at a later time point, and if the difference is a positive or zero difference (e.g., the quantitative measures of autoantibodies of the dataset at a panel of colorectal cancer-associated autoantibodies comprising quantitative measures of a panel of colorectal cancer-associated autoantibodies increased or remained at a constant level from the earlier time point to the later time point), and if an efficacious treatment was indicated at an earlier time point, then the difference may be indicative of a non-efficacy of the course of treatment for treating the colorectal cancer of the subject. A clinical action or decision may be made based at least in part on this indication of the non-efficacy of the course of treatment for treating the colorectal cancer of the subject, e.g., ending a current therapeutic intervention and/or switching to (e.g., prescribing) a different new therapeutic intervention for the subject. The clinical action or decision may comprise recommending the subject for a secondary clinical test to confirm the non-efficacy of the course of treatment for treating the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

Kits

The present disclosure provides kits for identifying or monitoring a cancer of a subject. A kit may comprise probes or primers for identifying a quantitative measure (e.g., indicative of a presence, absence, or relative amount) of sequences at each of a plurality of cancer-associated autoantibodies in a cell-free biological sample of the subject. A quantitative measure (e.g., indicative of a presence, absence, or relative amount) of a panel of autoantibodies in the cell-free biological sample may be indicative of one or more cancers. The probes may be selective for the autoantibodies in the cell-free biological sample. A kit may comprise instructions for using the probes to process the cell-free biological sample to generate datasets indicative of a quantitative measure (e.g., indicative of a presence, absence, or relative amount) of autoantibodies in a cell-free biological sample of the subject.

The probes in the kit may be selective for the sequences at the plurality of cancer-associated autoantibodies in the cell-free biological sample. The probes in the kit may be configured to selectively enrich autoantibody molecules corresponding to the plurality of cancer-associated autoantibodies. The probes in the kit may be proteins recognized by the autoantibodies and tagged to permit isolation after binding to the autoantibodies in the biological sample.

The instructions in the kit may comprise instructions to assay the cell-free biological sample using the probes that are selective for the cancer-associated autoantibodies in the cell-free biological sample. A quantitative measure (e.g., indicative of a presence, absence, or relative amount) of sequences at each of a plurality of cancer-associated autoantibodies in the cell-free biological sample may be indicative of one or more cancers.

The instructions in the kit may comprise instructions to measure and interpret assay readouts, which may be quantified at one or more of the plurality of cancer-associated autoantibodies to generate the datasets indicative of a quantitative measure (e.g., indicative of a presence, absence, or relative amount) of sequences at each of the plurality of cancer-associated autoantibodies in the cell-free biological sample.

EXAMPLES

Example 1: Autoantibody Analysis in Patient Plasma Samples

In cancer, autoantibodies whether to cancer neoantigens or canonical protein antigens represents a source of potential early diagnostic biomarkers for colorectal cancer. Autoantibodies are generated in response to protein overexpression or mutations in cancer patients. Some autoantibodies have been identified that are associated with breast, prostate, colorectal, lung, and ovarian cancers.

To identify autoantibodies that are informative for the methods and classifiers described herein, plasma from patients with colon cell proliferative disorders and plasma of subjects without colon cell proliferative disorders (control plasma or reference plasma) have been examined to identify a signature panel of autoantibodies produced by patients having a colon cell proliferative disorder in response to the colon cell proliferative disorder and respective reactive proteins. To that end, plasma from patients with colon cell proliferative disorders and control plasma were tested using high-density protein microarrays. Protein microarrays offer a series of advantages with respect to other approaches used for identifying autoantibodies: i) the proteins printed in the array are known beforehand, preventing a subsequent identification and eliminating the possible selection of mimotopes, and ii) there is no predisposition to select any protein because they are all printed at a similar concentration. This combination of factors results in a high sensitivity for identifying biomarkers.

The antibody panel identified allowed differentiation between plasma from subjects with a colon cell proliferative disorder and healthy subjects.

Methods

Sample Categorization

To detect autoantibodies in a plasma sample, high-density protein microarrays expressing several thousand candidate tumor antigens were probed with plasma drawn from subjects subsequently identified as having colorectal cancer (CRC), advanced adenoma (AA), benign polyp (NAA), or none of these (NEG). Bound immunoglobulin was measured by fluorescently-labeled secondary (anti-IgG/IgM) antibody intensity.

Plasma samples from age-, gender-, and location-matched general population control subjects were obtained using a standardized serum collection protocol and stored at −80° C. until use. Subjects with a personal history of cancer were excluded as controls. Written consent was obtained from all subjects under institutional review board approval.

A description of the study cohort is provided in TABLE 1, which shows the number of healthy and cancer samples used for CRC experiments in the classification model (by stage, gender, and age).

Plasma was isolated from subject samples representing NEG, CRC, AA, and NAA subject populations and screened on a protein array. A total of 42,390 features were identified between NEG, CRC, AA, and NAA subject populations and interrogated for differential expression in plasma from subjects with colon cell proliferative disorder and in healthy subject plasma.

Image analysis and quantification were performed using standard methodology previously described for protein array platforms. Briefly, slides were scanned using a two-channel microarray scanner and the spot foreground (spot area) and background (spot periphery) intensities measured. Raw intensity values were normalized by the following steps:
1) Remove background by subtracting median background intensities from foregrounds across all spots on the array (background corrected intensities).
2) Estimate parameters (mean, variance) of foreground/background normal+exponential convolutional model (assumes raw values represent the sum of background and foreground contributions) using negative control spot foreground intensities.
3) Subtract mean control spot intensity and coefficient of variation (control spot variance divided by protein foreground mean) from background corrected intensities.
4) Report background-corrected proteins intensities as the maximum likelihood estimation of the convolutional model.

Filtering on Raw Feature Values Upfront:

The raw feature values for both the IgG and IgM channels were concatenated into a single feature matrix for all cohort samples. This encompasses a total of 42,390 features across 941 samples (including unclassifiable).

After pre-processing (background correction, IQR median standardization, outlier trimming, and batch normalization), the feature space was narrowed to only those with a raw foreground intensity greater than 2000 (values range from 0 to 64000 rfu) in 10 or more samples. 16570 proteins/antigens met these criteria.

4-fold stratified cross validation was run across 5 random seeds using the following feature selection criteria (within each fold) for each indication (CRC, AA, NAA, vs. NEG):
A) Normalized values were binarized based on whether they were ≥2 standard deviations from the feature mean

TABLE 1

| | | CRC (n = 89) | AA (n = 127) | NAA (n = 150) | Control/NEG (n = 445) |
|---|---|---|---|---|---|
| Gender | Female 360 (44.4%) | 36 | 57 | 61 | 206 |
| | Male 451 (55.6%) | 53 | 70 | 89 | 239 |
| Age | Median, IQR | Median age: 65.0 IQR: 56.0-72.0 | Median age: 63.0 IQR: 55.5-70.0 | Median age: 65.5 IQR: 62.0-69.0 | Median age: 62.0 IQR: 46.0-67.0 |

The primary goal of this study was to identify serum TAAb biomarkers that would distinguish colorectal cancer from advanced adenoma, benign disease and healthy controls in order to improve the sensitivity of current biomarkers and guide clinical decisions. We performed a sequential screening strategy, in order to identify a panel of TAAb biomarkers from >21,000 human proteins (measured in duplicate).

B) Features were retained if their binarized chi2 p-values were ≤0.01 (binary values only used for chi2 comparison).
C) Retained features were subjected to recursive feature elimination by log reg weight, top 100 features were then used for CV classification in each fold.

Features were ranked by the number of times a feature was selected across all folds/sees (max 20), as well as the mean and sum of all log reg weights.

Results

CRC Vs. NEG

A total of 28 proteins (in supplement) were selected in ≥50% of all folds. TABLE 2 shows the top 5 AAb targets for CRC classification of the 28 proteins.

TABLE 2

| Protein | Ig_class |
|---|---|
| TP53 | IgG |
| MTCP1 | IgM |
| RBM38 | IgG |
| PRMT6 | IgM |
| CDK4 | IgM |

Figure 2:
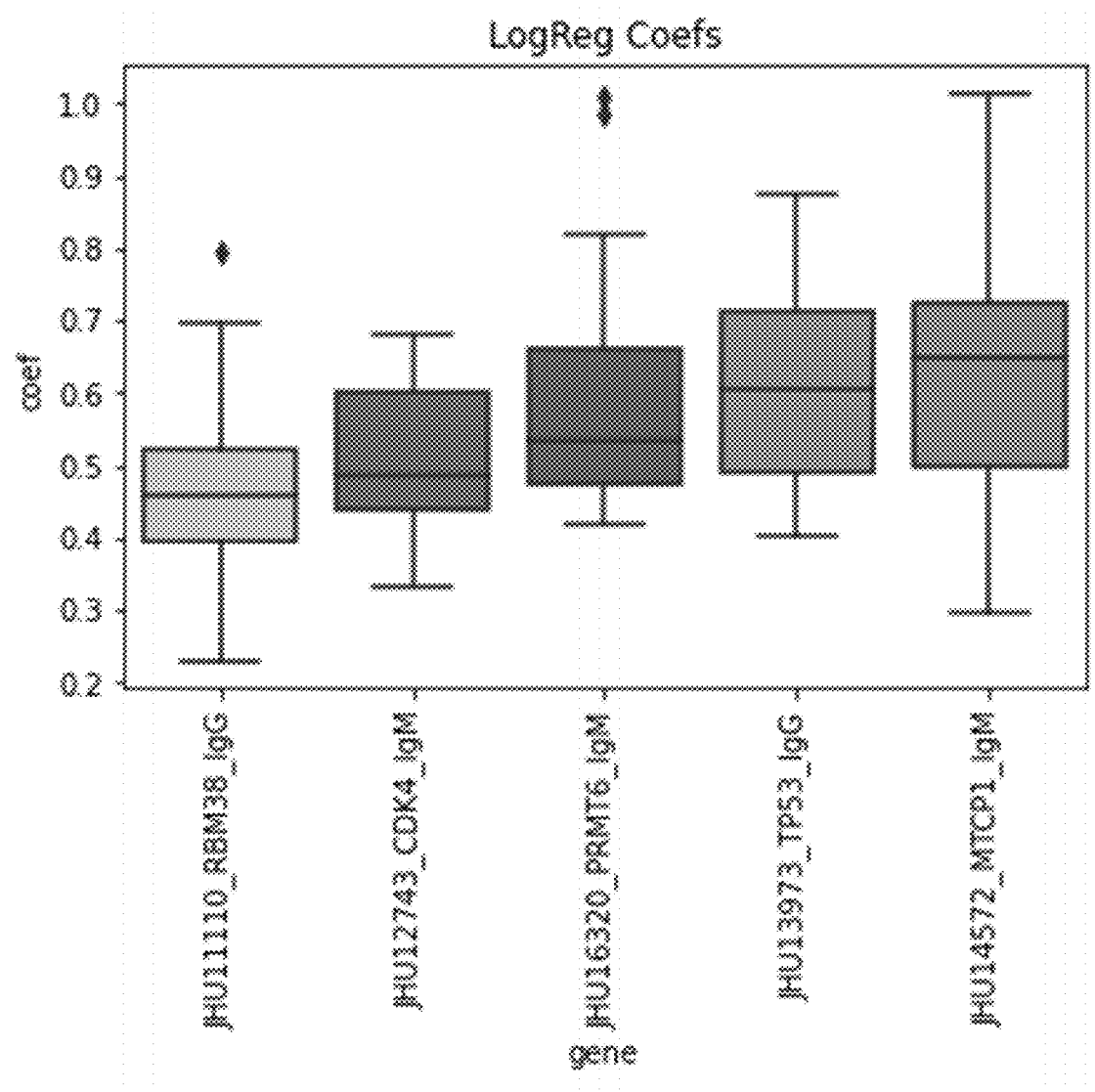
FIG. 2 provides a graph showing the CV coefficients of top 5 AAb targets for CRC classification.

FIG. 2 provides a graph showing CV coefficients of top 5 AAb targets chosen for potential development for CRC classification.

Figure 3:
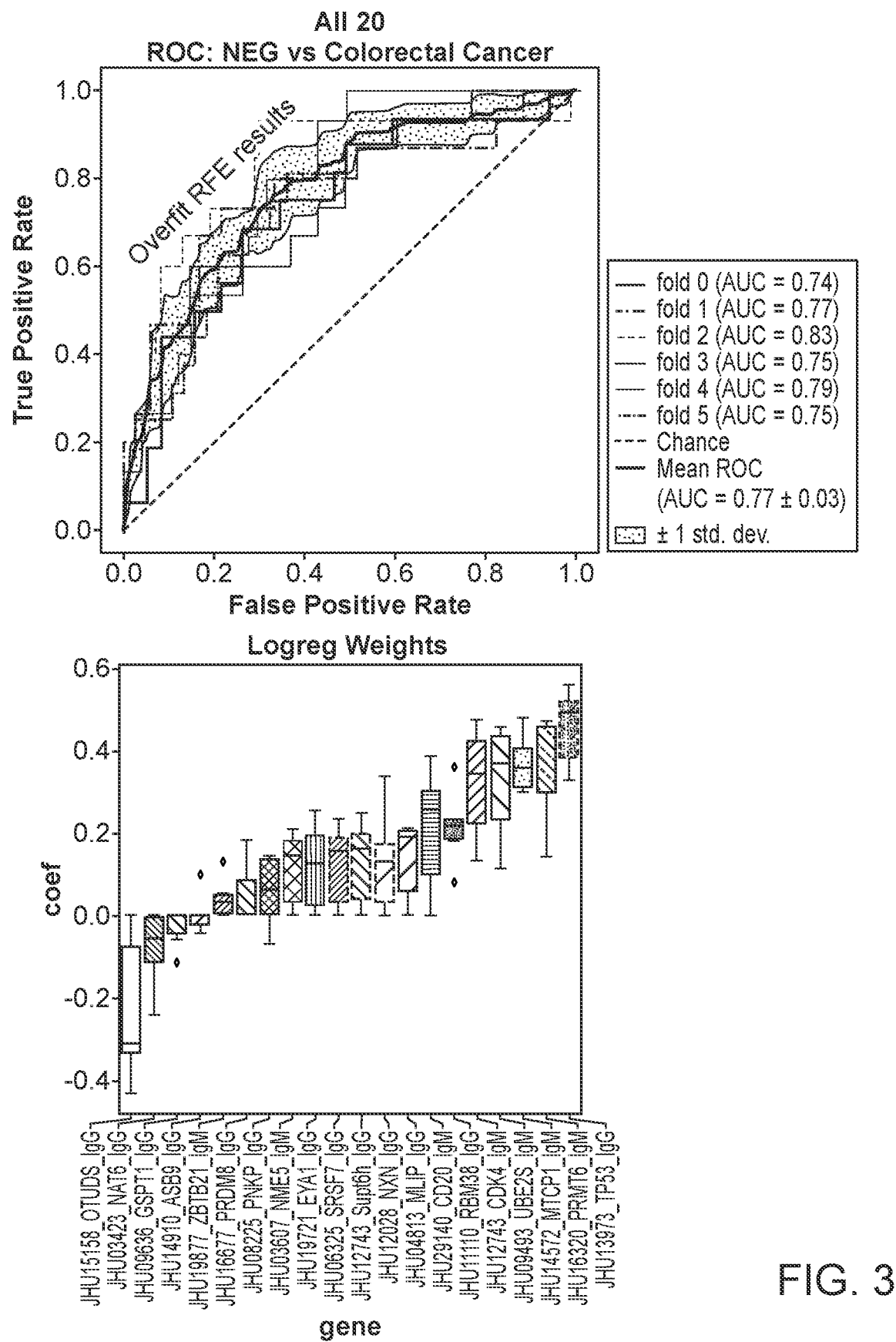
FIG. 3 provides graphs showing recursive feature elimination for CRC classification performance in CV.

FIG. 3 provides graphs showing recursive feature elimination for CRC classification performance in CV.

AA Vs. NEG

A total of 23 proteins (in supplement) were selected in ≥50% of all folds. TABLE 3 shows the top 5 AAb targets for AA classification of the 23 proteins.

TABLE 3

| Protein | Ig_class |
|---|---|
| CD20 | IgM |
| UBE2S | IgM |
| NME5 | IgM |
| Supt6h | IgG |
| PRDM8 | IgG |
| NAT6 | IgG |
| OTUD5 | IgG |
| SRSF7 | IgG |
| ASB9 | IgG |
| PNKP | IgG |

Figure 4:
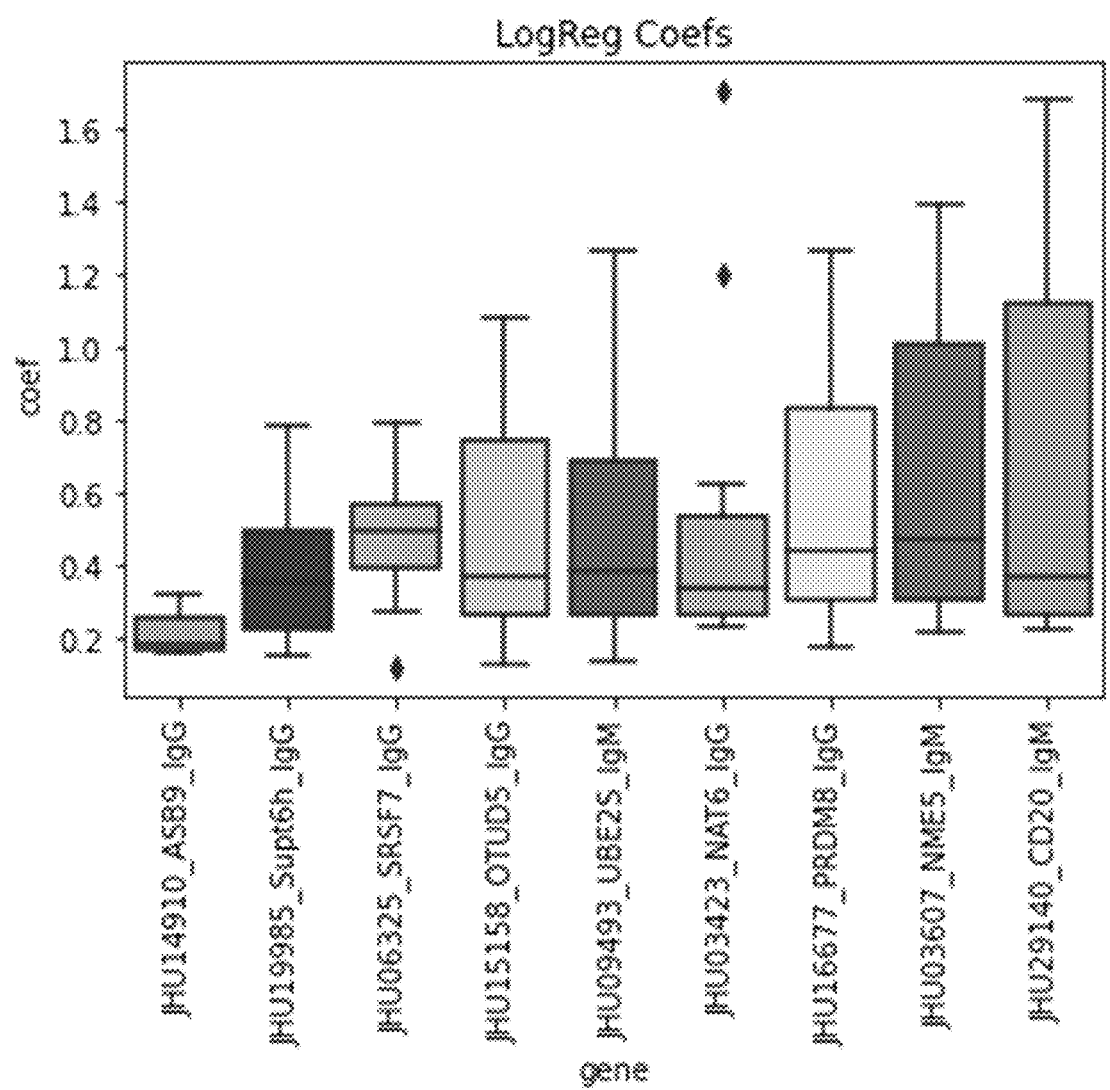
FIG. 4 provides a graph showing the CV coefficients of top 10 AAb targets for AA classification.

FIG. 4 provides a graph showing the CV coefficients of top 10 AAb targets for AA classification.

Figure 5:
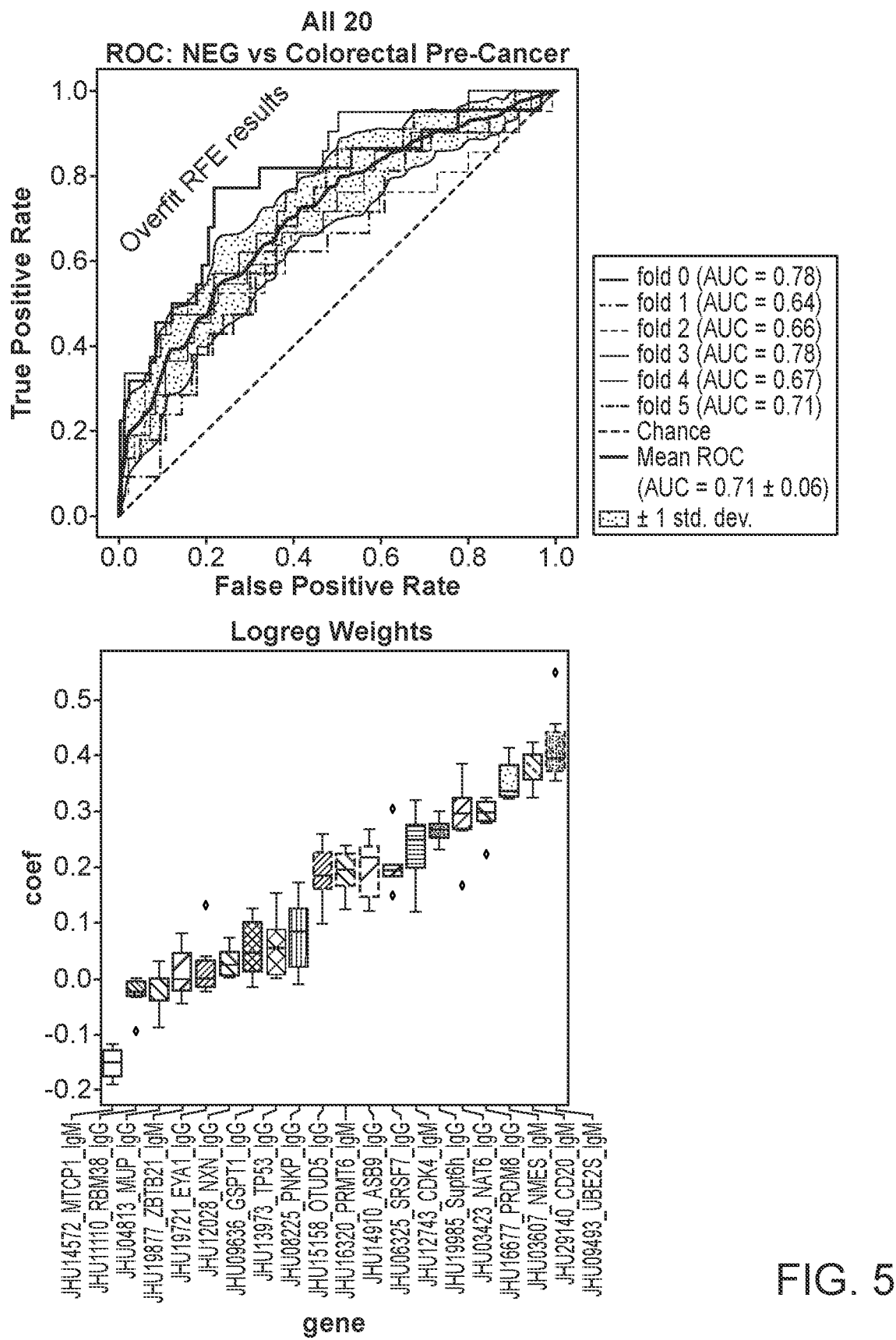
FIG. 5 provides graphs showing recursive feature elimination for AA classification performance in CV.

FIG. 5 provides graphs showing recursive feature elimination for AA classification performance in CV.

NAA Vs. NEG 13 targets met the selection criteria in >=50% of all folds. TABLE 4 shows the top 5 AAb targets for NAA classification of the 13 proteins.

TABLE 4

| Protein | Ig_class |
|---|---|
| NXN | IgG |
| ZBTB21 | IgM |
| EYA1 | IgG |
| GSPT1 | IgG |
| MLIP | IgG |

Figure 6:
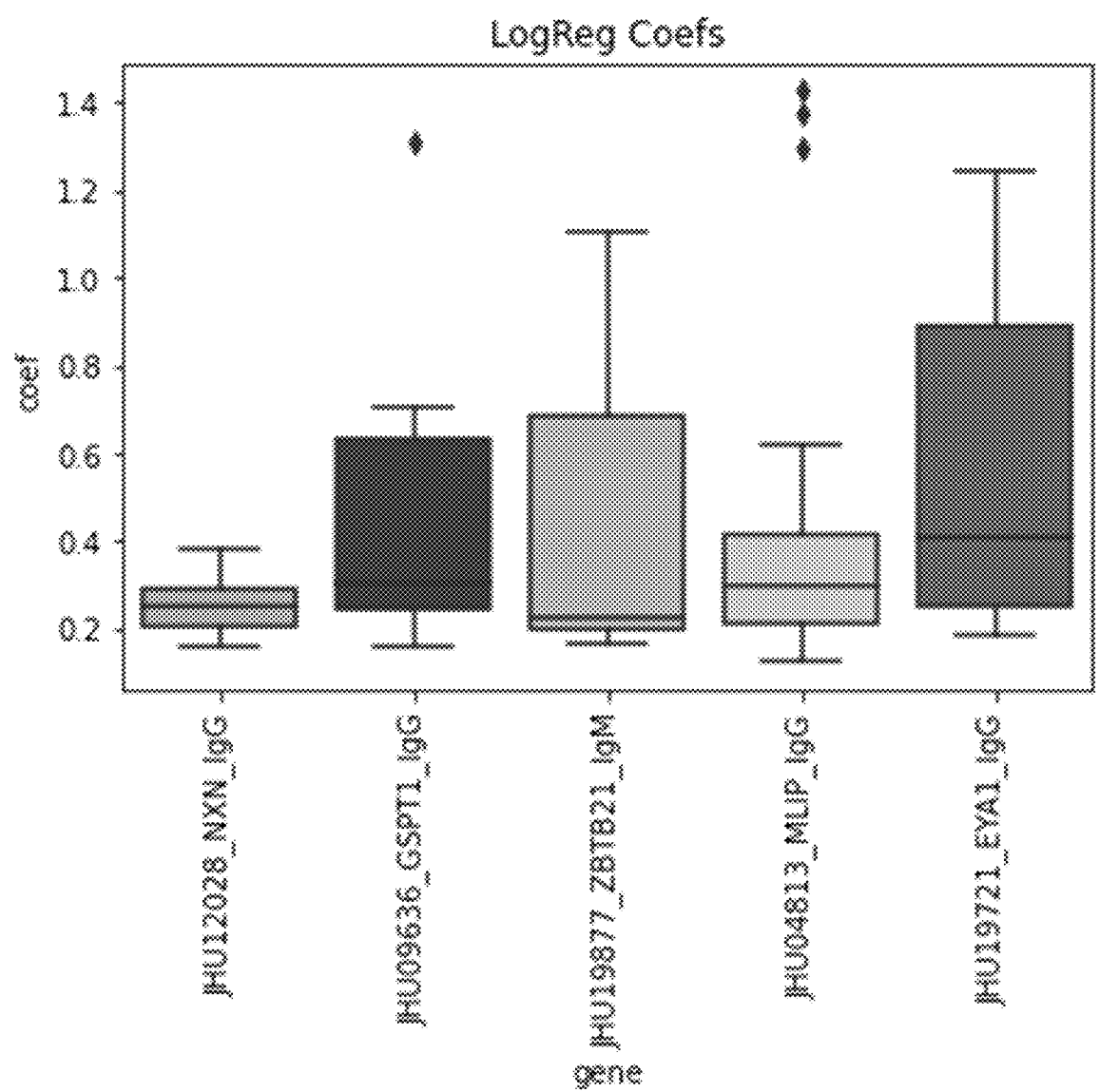
FIG. 6 provides a graph showing the CV coefficients of top 5 AAb targets for NAA classification.

FIG. 6 provides a graph showing the CV coefficients of top 5 AAb targets for NAA classification.

Figure 7:
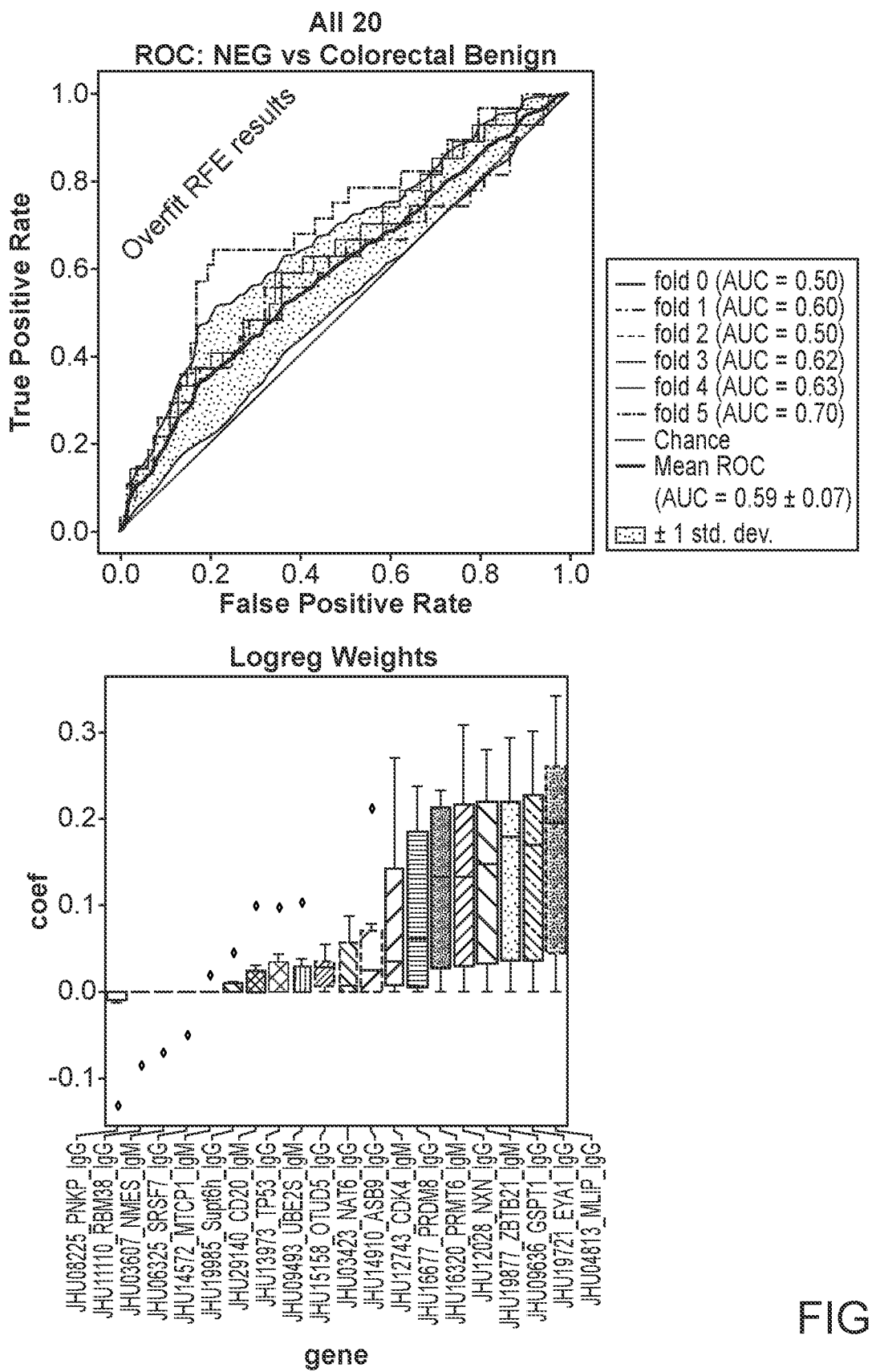
FIG. 7 provides graphs showing recursive feature elimination for NAA classification performance in CV.

FIG. 7 provides graphs showing recursive feature elimination for NAA classification performance in CV.

Together, the results provide a list of AAb biomarkers for classification of CRC, AA, and NAA as shown in TABLE 5.

TABLE 5

| Protein | Ig_class | Indication |
|---|---|---|
| TP53 | IgG | CRC |
| MTCP1 | IgM | CRC |
| RBM38 | IgG | CRC |
| PRMT6 | IgM | CRC |
| CDK4 | IgM | CRC |
| CD20 | IgM | AA |
| UBE2S | IgM | AA/CRC |
| NME5 | IgM | AA |
| Supt6h | IgG | AA |
| PRDM8 | IgG | AA/NAA |
| NAT6 | IgG | AA |
| OTUD5 | IgG | AA |
| SRSF7 | IgG | AA |
| ASB9 | IgG | AA |
| PNKP | IgG | AA |
| NXN | IgG | NAA |
| ZBTB21 | IgM | NAA |
| EYA1 | IgG | NAA |
| GSPT1 | IgG | NAA |
| MLIP | IgG | NAA |
| PCOLCE | IgM | CRC |
| SDCBP | IgM | AA |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forthherein which depend upon a variety of conditions and variables. It should be understood that various alternatives to the embodiments of the invention described herein may be employed in practicing an invention of the disclosure. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of treating a colorectal cancer in a subject, comprising:
   (a) obtaining an autoantibody profile of the subject, wherein the obtaining comprises assaying a biological sample obtained or derived from the subject to measure an amount of an autoantibody from a pre-determined set of autoantibodies, wherein the pre-determined set of autoantibodies comprises:
   (i) IgM autoantibodies to at least three antigens selected from the group consisting of NME5, USP16, UBE2S, RNF41, CD20, and SDCBP;
   (ii) IgM autoantibodies to at least three antigens selected from the group consisting of PELO, CDK4, MTP1, PRMT6, ZBTB2, and PCOLCE;
   (iii) IgG autoantibodies to at least three antigens selected from the group consisting of ANKHD1, TXNL1, NAT6, Supt6h, PRDM8, OTUD5, PNKP, SRSF7, PCOLCE, and ASB9;
- (iv) IgG autoantibodies to at least three antigens selected from the group consisting of TSSC4, BRD9, BCCIP, and TP53; or
- (v) a combination of (i) to (iv);
(b) detecting the colorectal cancer in the subject, wherein the detecting comprises processing, by a computer specifically programmed to detect the colorectal cancer, the autoantibody profile using a trained machine learning model, wherein the trained machine learning model has been trained to distinguish between subjects with the colorectal cancer and subjects without the colorectal cancer; and
(c) responsive to the detecting in (b), administering to the subject a treatment for the colorectal cancer, wherein the treatment is selected from the group consisting of surgery, radiofrequency ablation, chemotherapy, radiation therapy, targeted therapy, and immune therapy.

2. The method of claim 1, wherein the biological sample is selected from the group consisting of a body fluid, stool, colonic effluent, urine, blood plasma, blood serum, whole blood, isolated blood cells, cells isolated from the blood, tissue biopsy, and a combination thereof.

3. The method of claim 2, wherein the biological sample is the blood plasma.

4. The method of claim 1, wherein the colorectal cancer is selected from the group consisting of Lynch syndrome, colon cancer, rectal cancer, colorectal carcinoma, colorectal adenocarcinoma, carcinoid tumor, gastrointestinal carcinoid tumor, gastrointestinal stromal tumor (GIST), lymphoma, and sarcoma.

5. The method of claim 1, wherein the pre-determined set of autoantibodies further comprises (i) IgM autoantibodies to at least three antigens selected from the group consisting of NME5, USP16, UBE2S, RNF41, CD20, and SDCBP.

6. The method of claim 1, wherein the pre-determined set of autoantibodies further comprises (iii) IgG autoantibodies to at least three antigens selected from the group consisting of ANKHD1, TXNL1, NAT6, Supt6h, PRDM8, OTUD5, PNKP, SRSF7, PCOLCE, and ASB9.

7. The method of claim 1, wherein the pre-determined set of autoantibodies further comprises (ii) IgM autoantibodies to at least three antigens selected from the group consisting of PELO, CDK4, MTP1, PRMT6, ZBTB2, and PCOLCE.

8. The method of claim 1, wherein the pre-determined set of autoantibodies further comprises (iv) IgG autoantibodies to at least three antigens selected from the group consisting of TSSC4, BRD9, BCCIP, and TP53.

9. The method of claim 8, wherein the pre-determined set of autoantibodies further comprises IgG autoantibodies to TP53.

10. The method of claim 1, further comprising determining a methylation status of one or more nucleic acid molecules in the biological sample to provide a methylation profile of the subject.

11. The method of claim 10, wherein (b) further comprises processing the methylation profile using the trained machine learning model.

12. The method of claim 1, further comprising measuring an amount of one or more proteins in the biological sample to provide a protein profile of the subject.

13. The method of claim 12, wherein (b) further comprises processing the protein profile using the trained machine learning model.

* * * * *